(12) United States Patent
Gwag et al.

(10) Patent No.: US 6,573,402 B1
(45) Date of Patent: Jun. 3, 2003

(54) COMPOUNDS, COMPOSITIONS AND METHODS FOR PREVENTING NEURODEGENERATION IN ACUTE AND CHRONIC INJURIES IN THE CENTRAL NERVOUS SYSTEM

(75) Inventors: Byoung Joo Gwag, Seoul (KR); Young Ae Lee, Suwon-si (KR); Bo Rum Ryu, Suwon-si (KR); Sung Hwa Yoon, Suwon-si (KR); Ho Sang Moon, Suwon-si (KR)

(73) Assignee: Neurotech Co., Ltd., Kyungki-do (KR)

( * ) Notice: Subject to any disclaimer, the term of this patent is extended or adjusted under 35 U.S.C. 154(b) by 0 days.

(21) Appl. No.: 10/206,772

(22) Filed: Jul. 29, 2002

Related U.S. Application Data

(63) Continuation of application No. 09/557,001, filed on Apr. 20, 2000, now abandoned.

(51) Int. Cl.[7] ............................................. C07C 205/00

(52) U.S. Cl. ..................................................... 562/435

(58) Field of Search ........................................ 562/435

(56) References Cited

U.S. PATENT DOCUMENTS 3,632,760 A * 1/1972 Shen et al.

FOREIGN PATENT DOCUMENTS

| DE | 2 031 227 | 1/1971 |
|----|-----------|--------|
| EP | 122 827 | 10/1984 |
| GB | 1268465 | 3/1972 |
| JP | 54-125632 | 5/1979 |
| JP | 60-237041 | 4/1986 |
| WO | WO 86/03199 | 5/1986 |
| WO | WO 94/13663 | 6/1994 |

OTHER PUBLICATIONS

International Preliminary Examination Report for PCT/KR 00/00366, Aug. 23, 2002.
Anderson and Hall, *Ann.Emerg.Med.* 22:987–992 (1993).
Anderson, Swartzwelder, and Wilson, *J. Neurophysiol.* 57:1–21 (1987).
Beal, *Ann.Neurol.* 38:357–366 (1995).
Beal, Ferrante, Swartz, and Kowall, *J.Neurosci.* 11:1649–1659 (1991).
Beal, Kowall, Ellison, Mazurek, Swartz, and Martin, *Nature* 321: 168–171 (1986).
Brouillet and Beal. *Neuroreport.* 4:387–390 (1993).
Browne, Ferrante, and Beal, *Brain Pathol.* 9:147–163 (1999).
Bush, Pettingell, Multhaup, Paradis, Vonsattel, Gusella, Beyreuther, Masters, and Tanzi, *Science* 265:1464–1467 (1994).
Chan, *Stroke* 27:1124–1129 (1996).
Choi; *Neursci* 21:347–375 (1988).
Choi; *Neuron* 1:623–634 (1988).
Choi and Rothman, *Annu Rev Neurosci* 13:171–182 (1990).
Choi; *J Neurosci* 7:369–379, 1987.

(List continued on next page.)

*Primary Examiner*—Samuel Barts
*Assistant Examiner*—Paul A. Zucker
(74) *Attorney, Agent, or Firm*—Shanks & Herbert

(57) ABSTRACT

The present invention provides compositions and methods for prevention and prophylaxis of neurological diseases accompanied by neuronal death. The invention includes synthesis of 5-benzylamino salicylic acid (BAS) and its derivatives. BAS and its derivatives protect cortical neurons from toxic insults by N-methyl-D-aspartate, $Zn^{2+}$, and reactive oxygen species. Thus, the present invention provides compositions and methods for treating stroke, traumatic brain and spinal cord injury, epilepsy, and neurodegenerative diseases that are accompanied by severe neuronal loss via excitotoxicity, $Zn^{2+}$ neurotoxicity, and free radical neurotoxicity.

1 Claim, 38 Drawing Sheets

OTHER PUBLICATIONS

Cuajungco; *Brain Research Reviews* 23:219–236 (1997).

Demediuk, Daly, and Faden. J Neurochem J. *Neurochem.* 52:1529–1536 (1989).

Dingledine, McBain, and McNamara, *Trends.Pharmacol.Sci.* 11:334–338 (1990).

Eisen and Weber, *Drugs Aging* 14:173–196 (1999).

Faden, Demediuk, Panter, and Vink., *Science* 244:798–800 (1989).

Faden, Lemke, Simon, and Noble. *J.Neurotrauma.* 5:33–45(1988).

Faden, *Pharmacol.Toxicol.* 78:12–17 (1996).

Frederickson, Hernandez, and McGinty, *Brain Res.* 480:317–321 (1989).

Goldberg and Choi, 1993, J Neurosci. 13:3510–3524.

Goodman & Gilman's The Pharmacological Basis of Therapeutics, Joel G. Hardman et al., eds., 9$^{th}$ edition, 1996, The McGraw–Hill Companies, pps 617–631 & 1059–1062.

Grundman, *Am.J.Clin.Nutr.* 71:630S.–636S (2000).

Gwag BJ, Lobner D, Koh JY, Wie MB, and Choi DW, 1995, Neuroscience. 68:615–619.

Hall and Braughler, *Free Radic.Biol.Med.* 6:303–313 (1989).

Hall ,Braughler and McCall, *J. of Neurotrauma.* 5:81–89 (1988).

Hall, *Neurosurg.Clin.N.Am.* 8:195–206 (1997).

Holmes, *Cleve.Clin.J.Med.* 62:240–247 (1995).

Ikonomidou, Qin, Labruyere, and Olney *J.Neuropathol.Exp.Neurol.* 55:211–224 (1996).

Jenner and Olanow, *Neurology* 47:S161–S170 (1996).

Jenner, *Pathol. Biol.* (*Paris.*) 44:57–64 (1996).

Joo, et al, *IOVS* 40:713–720 (1999).

Kass, Chambers, and Cottrell, *Exp.Neurol.* 103:116–122 (1989).

Kim, et al, *European Journal of Neuroscience*, 11:327–334 (1999).

Koh and Choi, J Neurosci Methods 20:83–90, 1987.

Koh, Peter, and Choi, *Science* 234:73–76 (1986).

Koh, Suh, Gwag, He, Hsu and Choi, *Science* 272: 1013–1016 (1996).

Lakowski, Hekimi, *Science* 272. 1010–1016 (1996).

Lange, Loschmann, Sofic, Burg, Horowski, Kalveram, Wachtel, and Riederer, *Naunyn Schmiedebergs Arch.Pharmacol.* 348:586–592 (1993).

Lee, Zipfel, and Choi, *Nature* 399:A7–A14 (1999).

Love, *Brain Pathol.* 9:119–131 (1999).

Marin, Papa, Engber, Bonastre, Tolosa, and Chase, *Brain Res.* 736:202–205 (1996).

McNamara, Russell, Rigsbee, and Bonhaus, *Neuropharmacology* 27:563–568 (1988).

Merello, Nouzeilles, Cammarota, and Leiguarda. *Clin.Neuropharmacol.* 22:273–276 (1999).

Minta, Koa, Tsien, *J. of Biological Chemistry* vol. 264 14:8171–8178 (1989).

Montastruc,et al, *Neuroscience and Biobehavioral Reviews*, vol. 21 No. 4:477–480 (1997).

Okiyama, Smith, White, Richter, and McIntosh. *J.Neurotrauma.* 14:211–222 (1997).

Papa and Chase, *Ann.Neurol.* 39:574–578 (1996).

Park, Nehls, Graham, Teasdale, and McCulloch, *Ann Neurol* 24:543–551 (1988).

Prasad, Cole, and Kumar. *J.Am.Coll.Nutr.* 18:413–423 (1999).

Rosen, Siddique, Patterson, Figlewicz, Sapp, Hentiti, Donaldson, Goto, O'Regan, and Deng. *Nature* 362:59–62 (1993).

Rothstein. *Clin.Neurosci.* 3:348–359 (1995).

Schroder and Campbell, *Clin.Pharmacol.Ther.* 13:539–551 (1972).

Siesjo and Siesjo, *Eur.J.Anaesthesiol.* 13:247–268(1996).

Simon, Swan, Griffiths, and Meldrum. *Science* 226:850–852 (1984).

E. H. Sinz et al, *J. of Cerebral Blood Flow and Metabolism* 18:610–615 (1998).

Smith, Dawson, and Swan, *Gut* 20:802–805 (1979).

Smith, Harris, Sayre, and Perry, *Proc.Natl.Acad.Sci. U.S.A.* 94:9866–9868 (1997).

Stenson and Lobos, J. clin. Invest. 69, 494 (1982).

Suh, Chen, Motamedi, Bell, Listiak, Pons, Danscher, and Frederickson, *Brain Res.* 852 268–273 (2000).

Suh, Jensen, Jensen, Silva, Kesslak, Danscher, and Frederickson. *Brain Res.* 852:274–278 852 (2000).

Verhagen, Del Dotto, Natte, van den Munckhof, and Chase, *Neurology* 51:203–206 (1998).

Wahl, Liptay, Adler, and Schmid. *J. Clin.Invest.* 101:1163–1174 (1998).

Weiss JH, Hartley DM, Koh JY, Choi DW, 1993, Neuron. 10:43–49.

Weiss, Goldberg, and Choi, *Brain Res.* 380:186–190 (1986).

Wieloch, *Science* 230:681–683 (1985).

Won, *Neurobiology of Disease* 7:1–9 (2000).

Wong, Coulter, Choi, and Prince. *Neurosci.Lett.* 85:261–266 (1988).

Zeidman, Ling, Ducker, and Ellenbogen, *J.Spinal.Disord.* 9:367–380 (1996).

Mysyk, D. D. et al., Chloromethylation of 4–arenesulfonyl–N–methylamidoanisoles. Ukr. Khim. Zh. 33(2), 185–8 (1967)(Russ).

Nussbaumer, P. et al., Novel Antiproliferative Agents Derived from Lavendustin, A J. Med. Chem. 1994, 37(24), 4079–84 (Eng.).

PCT International Search Report, PCT/KR00–00366.

Rizzi, E. et al., Electron Impact Spectrometry of some 5–amin–osalicylic acid derivatives. Rapid Commun. Mass Spectrom. 1994, 8(2), 158–62 (Eng.).

* cited by examiner

COMPOUNDS, COMPOSITIONS AND METHODS FOR PREVENTING NEURODEGENERATION IN ACUTE AND CHRONIC INJURIES IN THE CENTRAL NERVOUS SYSTEM

This is a continuation of Application No. 09/557,001, filed Apr. 20, 2000 now abandoned, the entirety of which is/are incorporated by reference herein.

FIELD OF THE INVENTION

The present invention is related to novel salicylic compounds, compositions and methods for prevention and prophylaxis of neurological diseases accompanied by neuronal death.

BACKGROUND OF THE INVENTION

Excitotoxicity and Brain Diseases

Excess activation of ionotropic glutamate receptors sensitive to N-methyl-D-aspartate (NMDA receptors) produces neuronal death and has been known to mediate various neurological diseases [Choi, Neuron 1:623–634 (1988)]. Glutamate, the excitatory neurotransmitter, is massively accumulated in brain subjected to hypoxic-ischemic injuries, which activates ionotropic glutamate receptors permeable to $Ca^{2+}$ and $Na^+$ and then causes neuronal death [Choi and Rothman, Annu Rev Neurosci 13:171–182 (1990)]. Antagonists of NMDA receptors remarkably attenuate brain injury following hypoglycemia, hypoxia, or hypoxic-ischemia [Simon, Swan, Griffiths, and Meldrum. Science 226:850–852 (1984); Park, Nehls, Graham, Teasdale, and McCulloch, Ann Neurol 24:543–551 (1988).;Wieloch, Science 230:681–683 (1985); Kass, Chambers, and Cottrell, Exp. Neurol. 103:116–122 (1989); Weiss, Goldberg, and Choi, Brain Res. 380:186–190 (1986)]. Thus, NMDA receptor antagonists possess therapeutic potentials to protect brain against hypoglycemia, hypoxia, and hypoxic-ischemic injuries.

Excitotoxicity appears to contribute to neuronal degeneration following traumatic brain injury (TBI). Levels of quinolinic acid, an endogenous agonist of NMDA receptors, was increased 5- to 50-fold in human patients with TBI [E. H. Sinz, P. M. Kochanek, M. P. Heyes, S. R. Wisniewski, M. J. Bell, R. S. Clark, S. T. DeKosky, A. R. Blight, and D. W. Marion]. Quinolinic acid is increased in the cerebrospinal fluid and associated with mortality after TBI in humans [J. Cereb. Blood Flow Metab. 18:610–615, (1998)]. In animal models of brain trauma, levels of glutamate and aspartate were markedly increased [Faden, Demediuk, Panter, and Vink, Science 244:798–800 (1989)]. Glutamate release was also observed in rat spinal cord following impact trauma [Demediuk, Daly, and Faden. J Neurochem J. Neurochem. 52 :1529–1536 (1989)]. NMDA receptor antagonists attenuate neuronal death following traumatic brain or spinal cord injuries [Faden, Lemke, Simon, and Noble. J. Neurotrauma. 5:33–45 (1988); Okiyama, Smith, White, Richter, and McIntosh. J. Neurotrauma. 14:211–222 (1997)].

Glutamate plays a central role in the induction and the propagation of seizures [Dingledine, McBain, and McNamara, Trends. Pharmacol. Sci. 11:334–338 (1990); Holmes. Cleve. Clin. J. Med. 62:240–247 (1995)]. NMDA receptor antagonists were shown to act as anticonvulsants and antiepileptogenic drugs in various models of epilepsy [Anderson, Swartzwelder, and Wilson, J. Neurophysiol. 57:1–21 (1987); Wong, Coulter, Choi, and Prince. Neurosci. Lett. 85:261–266 (1988); McNamara, Russell, Rigsbee, and Bonhaus, Neuropharmacology 27:563–568 (1988)].

Amyotrophic lateral sclerosis (ALS) is accompanied by degeneration of both upper and lower motor neurons and marked by neurogenic atrophy, weakness, and fasciculation. While the pathogenesis of ALS remains to be resolved, excitotoxicity has been expected to participate in the process of ALS. In particular, ALS patients show increased levels of extracellular glutamate and defects in glutamate transport. Administration of excitotoxins mimicked pathological changes in the spinal cord of ALS patients [Rothstein. Clin. Neurosci. 3:348–359 (1995); Ikonomidou, Qin, Labruyere, and Olney J. Neuropathol. Exp. Neurol. 55:211–224 (1996)].

Antagonizing NMDA receptors appears to be applied to treat Parkinson's disease (PD). Several antagonists of NMDA receptors protect dopaminergic neurons from the neurotoxin MPTP (1-methyl-4-phenyl-1,2,3,6-tetrahydropyridine) [Lange, Loschmann, Sofic, Burg, Horowski, Kalveram, Wachtel, and Riederer. Naunyn Schmiedebergs Arch. Pharmacol. 348:586–592 (1993); Brouillet and Beal. Neuroreport. 4:387–390 (1993)]. NMDA receptor antagonists also ameliorate levodopa-induced dyskinesia and thus can improve the therapeutic effects of levodopa [Papa and Chase, Ann. Neurol. 39:574–578 (1996); Marin, Papa, Engber, Bonastre, Tolosa, and Chase, Brain Res. 736:202–205 (1996)]. Two NMDA receptor antagonists, memantine and dextromethophan, have been proved beneficial in treating PD patients [Verhagen, Del Dotto, Natte, van den Munckhof, and Chase, Neurology 51:203–206 (1998); Merello, Nouzeilles, Cammarota, and Leiguarda. Clin. Neuropharmacol. 22:273–276 (1999)].

Huntington's disease (HD) is a progressive neurodegenerative disease predominantly affecting small- and medium-sized interneurons but sparing NADPH-diaphorase neurons containing somatostatin and neuropeptide in the striata. These pathological features of HD are observed in the striatal tissues following the intrastriatal injections of quinolinic acid or cultured striatal neurons exposed to NMDA, raising the possibility that NMDA receptor-mediated neurotoxicity contributes to selective neuronal death in HD [Koh, Peters, and Choi, Science 234:73–76 (1986); Beal, Kowall, Ellison, Mazurek, Swartz, and Martin, Nature 321:168–171 (1986); Beal, Ferrante, Swartz, and Kowall. J. Neurosci. 11:1649–1659 (1991)].

Free radicals and Brain Diseases

Free radicals are produced in degenerating brain areas following hypoxic-ischemia or traumatic brain and spinal cord injuries [Hall and Braughler, Free Radic. Biol. Med. 6:303–313 (1989); Anderson and Hall, Ann. Emerg. Med. 22:987–992 (1993); Siesjo and Siesjo, Eur. J. Anaesthesiol. 13:247–268 (1996); Love, Brain Pathol. 9:119–131 (1999)]. Antioxidants or maneuvers scavenging free radicals attenuate brain damages by hypoxic-ischemia or traumatic injuries [Faden, Pharmacol. Toxicol. 78:12–17 (1996); Zeidman, Ling, Ducker, and Ellenbogen, J. Spinal. Disord. 9:367–380 (1996); Chan, Stroke 27:1124–1129 (1996); Hall, Neurosurg. Clin. N. Am. 8:195–206 (1997)]. Extensive evidence supports that free radicals can be produced in brain areas undergoing degeneration in neurodegenerative diseases possibly due to point mutations in Cu/Zn superoxide dismutase in ALS, decreased glutathione and increased iron in PD, accumulation of iron in AD, or mitochondrial dysfunction in HD [Rosen, Siddique, Patterson, Figlewicz, Sapp, Hentati, Donaldson, Goto, O'Regan, and Deng. Nature 362:59–62 (1993); Jenner and Olanow, Neurology 47:S161–S170 (1996); Smith, Harris, Sayre, and Perry, Proc. Natl. Acad. Sci. U.S.A. 94:9866–9868 (1997); Browne, Ferrante, and Beal, Brain Pathol. 9:147–163 (1999)]. Accordingly, antioxidants have been neuroprotective against such neurodegenerative diseases [Jenner, Pathol. Biol. (Paris.) 44:57–64 (1996); Beal, Ann. Neurol. 38:357–366 (1995); Prasad, Cole, and Kumar. J. Am. Coll. Nutr. 18:413–423 (1999); Eisen and Weber, Drugs Aging 14:173–196 (1999); Grundman, Am. J. Clin. Nutr. 71:630S.-636S (2000)].

Zinc and Brain Diseases $Zn^{2+}$ mediates neurodegenerative process observed in seizure, ischemia, trauma, and Alzheimers disease (AD). The central administration of kainate, a seizure-inducing excitotoxin, causes the translocation of $Zn^{2+}$ into postsynaptic degenerating neurons in several forebrain areas [Frederickson, Hernandez, and McGinty. Brain Res. 480:317–321 (1989)]. Blockade of $Zn^{2+}$ translocation with Ca-EDTA attenuates neuronal loss following a transient forebrain ischemia or traumatic brain injury [Koh, Suh, Gwag, He, Hsu and Choi, Science 272:1013–1016 (1996); Suh, Chen, Motamedi, Bell, Listiak, Pons, Danscher, and Frederickson, Brain Res. 852 :268–273 (2000)]. $Zn^{2+}$ is observed in the extracellular plaque and degenerating neurons in AD, which likely contributes to neuronal degeneration in AD [Bush, Pettingell, Multhaup, Paradis, Vonsattel, Gusella, Beyreuther, Masters, and Tanzi, Science 265:1464–1467 (1994); Suh, Jensen, Jensen, Silva, Kesslak, Danscher, and Frederickson. Brain Res. 852:274–278 852 (2000)].

SUMMARY OF THE INVENTION

The present invention provides novel 5-benzylamino salicylic acid (BAS) and its derivatives represented by the following formula (I):

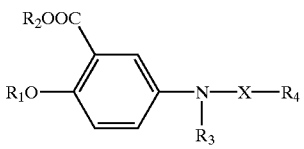

(I)

wherein,

X is CO, $SO_2$ or $(CH_2)_n$ (where n is an integer of 1 to 5, inclusive);

$R_1$ is hydrogen, alkyl or alkanoyl;

$R_2$ is hydrogen or alkyl;

$R_3$ is hydrogen or an acetoxy group; and $R_4$ is phenyl group which is unsubstituted or substituted with one or more of the group consisting of nitro, halogen, haloalkyl, and $C_1$–$C_5$ alkoxy; or a pharmaceutically-acceptable salt thereof.

The present invention also provides method for protecting central neurons from acute or chronic injuries to central nervous system (CNS), comprising administering to a patient or a mammal suffering from such CNS injuries a therapeutically appropriate amount of a neuroprotective compound represented by Formula (I).

The present invention still provides a composition for protecting central neurons from acute or chronic injuries to central nervous system comprising a neuroprotective compound represented by Formula (I) in a therapeutically appropriate amount.

The present invention still provides a method for treating or preventing neurological diseases linked to NMDA neurotoxocity, $Zn^{2+}$ neurotoxicity or oxidative stress, comprising administering to a patient or a mammal suffering from such diseases a therapeutically effective amount of the compound represented by Formula (I).

The present invention more provides a use of the compound of Formula (I) in the manufacture of medicaments for protecting central neurons from acute or chronic injuries to central nervous system (CNS).

The above and other features of the present invention will be apparent to those of ordinary skill in the art from the detailed description.

DETAILED DESCRIPTION OF THE INVENTION

Figure 1A:
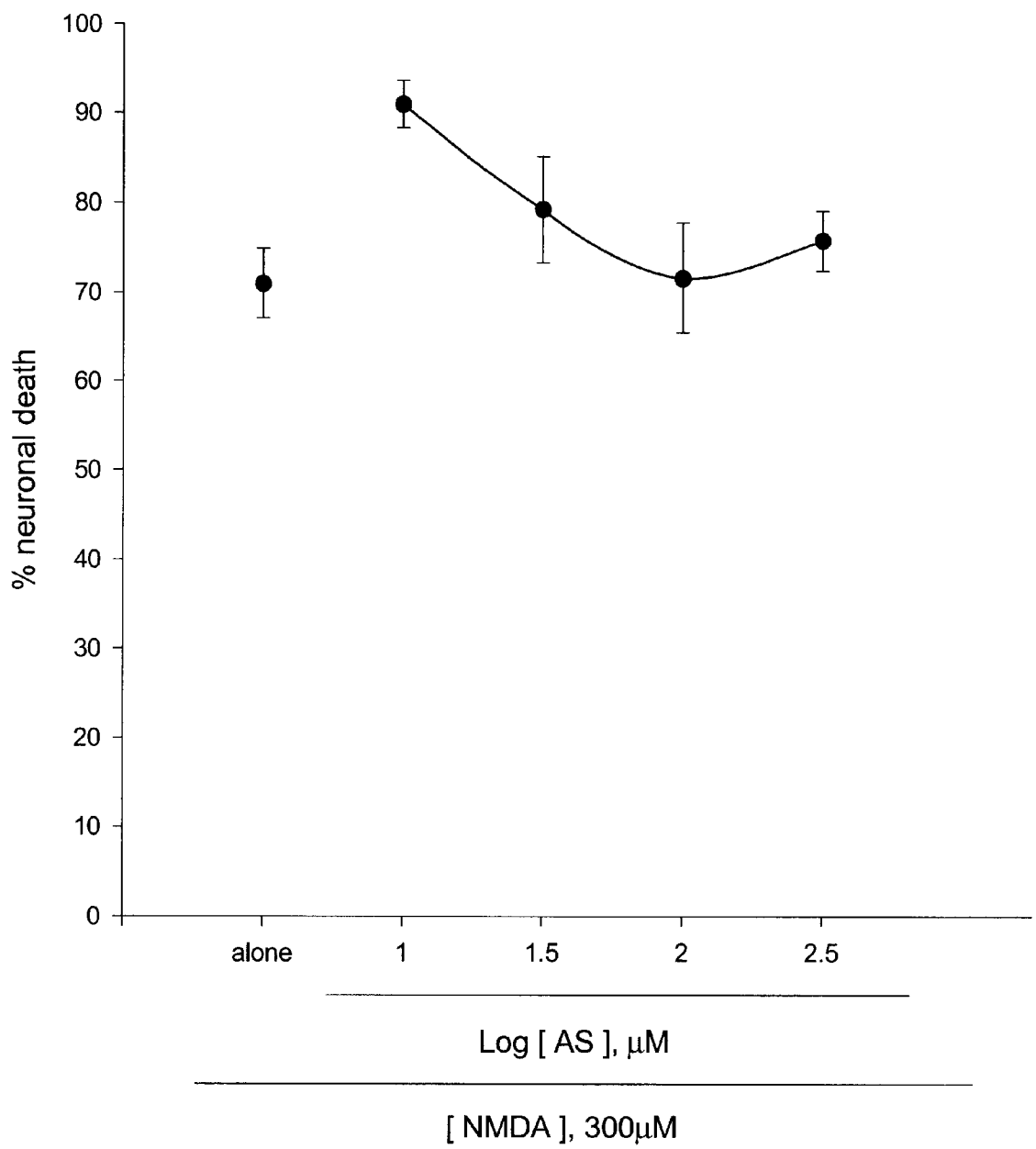
FIG. 1 is a result testing neuroprotective effects of 5-amino salicylic acid (AS) against neuronal death induced by an excitotoxin NMDA (1a), a free radical-producing agent Fe2+ (1b) or Zn2+ (1c) in cultured cortical cells.

We have synthesized 5-benzylamino salicylic acid (BAS) and its derivatives and demonstrated that these synthetic compounds have multiple neuroprotective action. First, BAS and its derivatives attenuate NMDA neurotoxicity at doses of 100–1,000 uM. Second, BAS and its derivatives are antioxidants and block free radical neurotoxicity at doses of 1–300 uM. Finally, BAS and its derivatives attenuate $Zn^{2+}$ neurotoxicity. These novel and multiple neuroprotective effects of BAS and its derivatives are merited to treat stroke, traumatic brain and spinal cord injury, epilepsy, and neurodegenerative diseases that are accompanied by excitotoxicity, $Zn^{2+}$ neurotoxicity, and free radical neurotoxicity.

The BAS and its derivatives may be synthesized from 5-aminosalicylic acid by reacting it with an appropriate compound. The following reaction schemes illustrate the synthesis of BAS and its derivatives.

$C_1$–$C_5$ alkyl or $C_2$–$C_5$ alkanoyl; $R_2$ is hydrogen or $C_1$–$C_5$ alkyl; $R_3$ is hydrogen or an acetoxy group; and $R_4$ is phenyl group which is unsubstituted or substituted with one or more selected from the group consisting of nitro, halogen, haloalkyl, and $C_1$–$C_5$ alkoxy; or a pharnaceutically-acceptable salt thereof.

Reaction Scheme 1

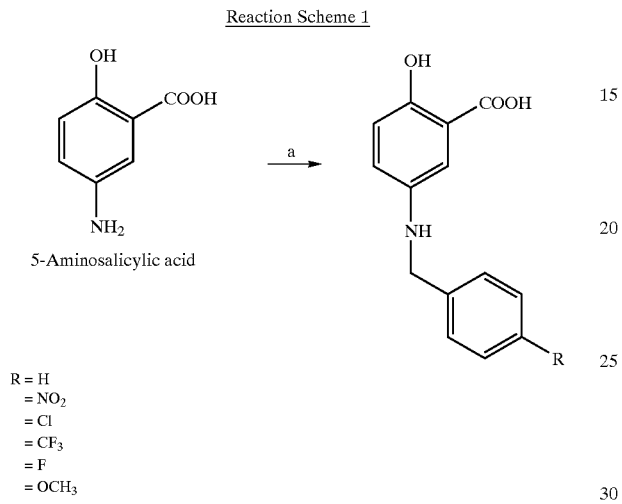

R = H
 = $NO_2$
 = Cl
 = $CF_3$
 = F
 = $OCH_3$

Reagents (a): Benzyl bromide, 4-nitrobenzyl bromide, 4-chlorobenzyl chloride, 4-(trifluoro methyl)benzyl chloride, 4-fluorobenzyl bromide, 4-methoxybenzyl chloride, N,N-dimethyl foramide (DMF), triethylamine, room temperature, 4 hr.

A preferred class of compounds within Formula (I) comprises those compounds wherein X is CO, $SO_2$ or $(CH_2)_n$ (where n is an integer of 1–5, inclusive); $R_1$ is hydrogen, Reaction Scheme 2

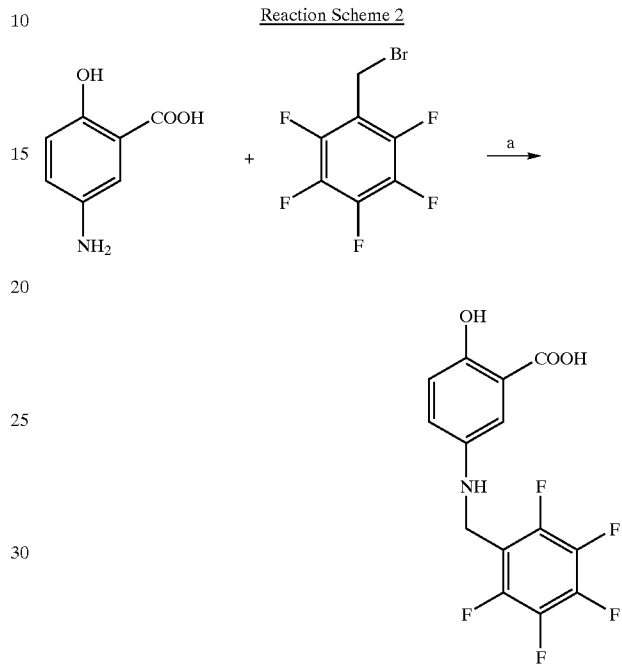

Reagents (a): N,N-dimethylforamide (DMF), triethylamine, room temperature, 4 hr.

Reaction Scheme 3

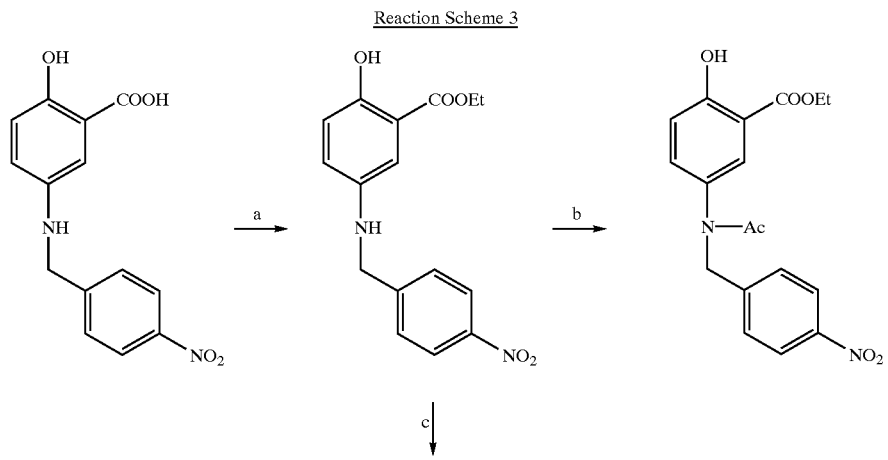

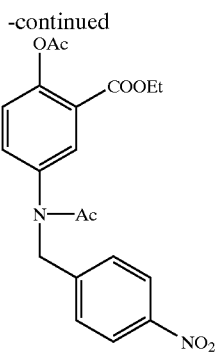

Reagents (a) EtOH, H$_2$SO$_4$, reflux, 6 hr.

(b) Acetic anhydride, MeOH, 0° C., 30 min.

(c) Acetic anhydride, H$_2$SO$_4$, 0° C., 30 min.

A more preferred class of compounds within Formula (I) encompasses those compounds wherein X is CO, SO$_2$ or (CH$_2$)$_n$ (where n=1,2,3); R$_1$ is hydrogen, C$_1$–C$_3$ alkyl or C$_2$–C$_3$ alkanoyl; R$_2$ is hydrogen or C$_1$–C$_3$ alkyl; R$_3$ is hydrogen or an acetoxy group; R$_4$ is phenyl group which is unsubstituted or substituted with one or more selected from the group consisting of nitro, halogen, halo(C$_1$–C$_3$)alkyl and C$_1$–C$_3$ alkoxy; or a pharmaceutically-acceptable salt thereof.

EXAMPLE 5

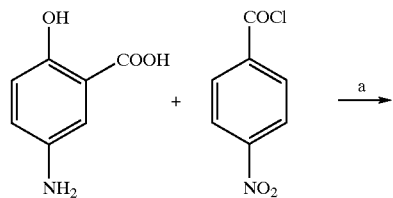

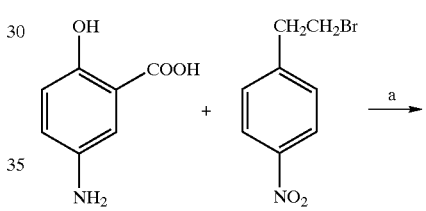

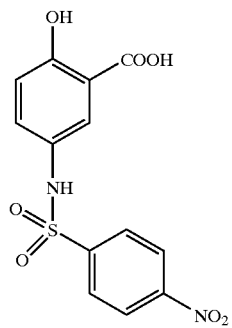

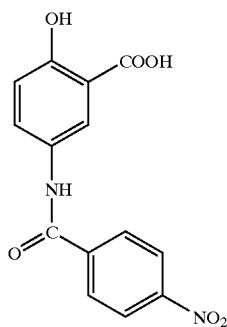

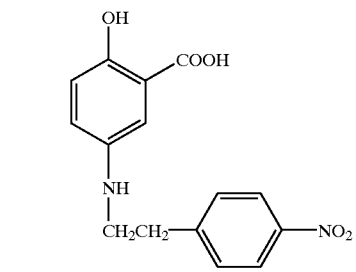

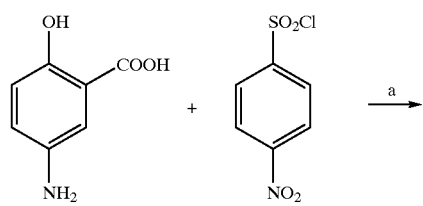

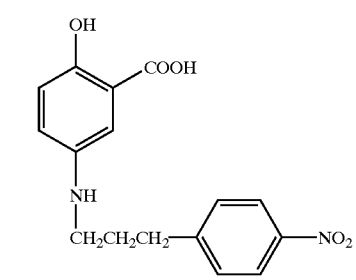

Reagents (a) N,N-dimethylforamide (DMF), triethylamine, room temperature, 4 hr.

Specific compounds of interest within Formula (I) are as follows:

5-benzylaminosalicylic acid (BAS), 5-(4-nitrobenzyl)aminosalicylic acid (NBAS), (5-(4-chlorobenzyl)aminosalicylic acid (CBAS), (5-(4-trifluoromethylbenzyl)aminosalicylic acid (TBAS), (5-(4-fluorobenzyl)aminosalicylic acid (FBAS), 5-(4-methoxybenzyl)aminosalicylic acid (MBAS)

5-(pentafluorobenzyl)aminosalicylic acid (PBAS), 5-(4-nitrobenzyl)amino-2-hydroxy ethylbenzoate (NAHE), 5-(4-nitrobenzyl)-N-acetylamino-2-hydroxy ethylbenzoate(NNAHE), 5-(4-nitrobenzyl)-N-acetylamino-2-acetoxy ethylbenzoate(NNAAE), 5-(4-nitrobenzoyl)aminosalicylic acid(NBAA), 5-(4-nitrobenzenesulfonyl)aminosalicylic acid(NBSAA), 5-[2-(4-nitrophenyl)-ethyl]aminosalicylic acid(NPAA), and 5-[3-(4-nitrophenyl)-n-propyl]aminosalicylic acid (NPPAA), or a pharmaceutically-acceptable salt thereof.

The term "pharmaceutically-acceptable salts" embraces salts commonly used to form alkali metal salts and to form addition salts of free acids or free bases. The nature of the salt is not critical, provided that it is pharmaceutically acceptable, and acids or bases which may be employed to form such salts are, of course, well known to those skilled in the art. Examples of acids which may be employed to form pharmaceutically acceptable acid addition salts include such inorganic acids as hydrochloric acid, sulfuric acid and phosphoric acid and such organic acids as maleic acid, succinic acid and citric acid. Other salts include salts with alkali metals or alkaline earth metals, such as sodium, potassium, calcium and magnesium, or with organic bases, such as dicyclohexylamine. All of these salts may be prepared by conventional means from the corresponding compound of Formula (I) by reacting, for example, the appropriate acid or base with the compound of Formula (I).

The Synthesis Examples show the exemplary method for the preparation of the representative compounds (I).

SYNTHESIS EXAMPLE 1

Preparation of 5-Benzylaminosalicylic Acid (BAS)

To a solution of 5-aminosalicylic acid (2.0 g, 13 mmole), purchased from Aldrich Chemical Company, USA) and triethylamine in dried DMF (25 ml) was added benzyl bromide (2.68 g, 1.90 ml, 15.6 mmole) at room temperature under a nitrogen atmosphere. The reaction mixture was stirred for 4 hr at room temperature. Ice chips were added to the reaction mixture and then solvent was removed in vacuo. The reaction mixture was diluted with water and then extracted with ethyl acetate. The organic layer was washed with water and brine, and then dried over anhydrous MgSO$_4$. After evaporation of the solvent, the residue was purified by column chromatography and recrystallized from methanol/ethyl acetate/hexane (1:3:1), to give 3.6 g (73% yield) of 5-benzylaminosalylic acid as a white solid.: mp 173.5–174.5° C. (decompose).

Elemental analysis for $C_{14}H_{13}NO_3$.

|  | % C | % H | % N |
| --- | --- | --- | --- |
| Calculated | 69.12 | 5.39 | 5.76 |
| Found | 69.30 | 5.18 | 5.63 |

SYNTHESIS EXAMPLE 2

Preparation of 5-(4-Nitrobenzyl)aminosalicylic Acid (NBAS)

By following the similar procedure in Synthesis Example 1 by using 5-aminosalicylic acid (2.00 g, 13.0 mmole) and 4-nitrobenzyl bromide (3.38 g, 15.6 mmole), 2.90 g (79% yield) of 5-(4-nitrobenzyl)aminosalicylic acid was obtained as a pale yellow solid.: mp 211–212° C.

Elemental analysis for $C_{14}H_{13}N_2O_5$.

|  | % C | % H | % N |
| --- | --- | --- | --- |
| Calculated | 58.33 | 4.20 | 9.72 |
| Found | 58.38 | 4.21 | 9.71 |

SYNTHESIS EXAMPLE 3

Preparation of 5-(4-Chlorobenzyl)aminosalicylic Acid (CBAS)

By following the similar procedure in Synthesis Example 1 by using 5-aminosalicylic acid (500 mg, 3.26 mmole) and 4-chlorobenzyl chloride (630 mg, 3.91 mmole), 480 mg (53% yield) of 5-(4-chlorobenzyl)aminosalicylic acid was obtained as a white solid.: mp 227–228° C.

Elemental analysis for $C_{14}H_{12}ClNO_3$.

|  | % C | % H | % N |
| --- | --- | --- | --- |
| Calculated | 60.55 | 4.36 | 5.04 |
| Found | 60.43 | 4.21 | 5.02 |

SYNTHESIS EXAMPLE 4

Preparation of 5-(4-Trifluoromethylbenzyl) aminosalicylic Acid (TBAS)

By following the similar procedure in Synthesis Example 1 by using 5-aminosalicylic acid (500 mg, 3.26 mmole) and 4-(trifluoromethyl)benzyl chloride (760 mg, 3.92 mmole), 510 mg (50% yield) of 5-(4-(trifluoromethyl)benzyl) aminosalicylic acid was obtained as a white solid.: mp>188° C. (decompose).

Elemental analysis for $C_{14}H_{12}F_3NO_3$.

|  | % C | % H | % N |
| --- | --- | --- | --- |
| Calculated | 57.88 | 3.89 | 4.50 |
| Found | 57.61 | 3.98 | 4.44 |

SYNTHESIS EXAMPLE 5

Preparation of 5-(4-Fluorobenzyl)aminosalicylic Acid (FBAS)

By following the similar procedure in Synthesis Example 1 by using 5-aminosalicylic acid (500 mg, 3.26 mmole) and 4-fluorobenzyl bromide (740 mg, 3.92 mmole), 480 mg (44% yield) of 5-(4-fluorobenzyl)aminosalicylic acid was obtained as a white solid.: mp>210° C. (decompose).

Elemental analysis for $C_{14}H_{12}FNO_3$.

|  | % C | % H | % N |
|---|---|---|---|
| Calculated | 64.36 | 4.63 | 5.36 |
| Found | 64.10 | 4.42 | 5.07 |

SYNTHESIS EXAMPLE 6

Preparation of 5-(4-Methoxybenzyl)aminosalicylic Acid (MBAS)

By following the similar procedure in Synthesis Example 1 by using 5-aminosalicylic acid (1.00 g, 6.53 mmole) and 4-methoxybenzyl chloride (1.23 g, 7.84 mmole), 890 mg (50% yield) of 5-(4-methoxybenzyl)aminosalicylic acid was obtained as a white solid.: mp 205–206° C.

Elemental analysis for $C_{15}H_{15}NO_4$.

|  | % C | % H | % N |
|---|---|---|---|
| Calculated | 65.92 | 5.53 | 5.13 |
| Found | 65.83 | 5.45 | 5.07 |

SYNTHESIS EXAMPLE 7

Preparation of 5-(Pentafluorobenzyl)aminosalicylic Acid

By following the similar procedure in Synthesis Example 1 by using 5-aminosalicylic acid (500 mg, 3.26 mmole) and pentafluorobenzyl bromide (1.02 g, 3.92 mmole), 650 mg (60% yield) of 5-(pentafluorobenzyl)aminosalicylic acid was obtained as a white solid.: mp>190° C. (decompose).

Elemental analysis for $C_{14}H_8F_5NO_3$.

|  | % C | % H | % N |
|---|---|---|---|
| Calculated | 50.46 | 2.42 | 4.20 |
| Found | 50.53 | 2.19 | 4.23 |

SYNTHESIS EXAMPLE 8

Preparation of 5-(4-Nitrobenzyl)amino-2-hydroxy Ethylbenzoate

To a solution of 5-(4-nitrobenzyl)aminosalicylic acid (1.0 g, 3.4 mmole) in ethanol (35 ml) was carefully added Conc.$H_2SO_4$ (3.5 ml) at 0° C. The reaction mixture was stirred for 6 hr at 80° C. and cooled to room temperature. After the solvent was removed in vacuo, the reaction mixture was extracted with ethyl acetate. The organic layer was washed with $H_2O$, 10% $NaHCO_3$ solution, 5% HCl solution and brine. After the organic layer was dried over anhydrous $MgSO_4$, it was concentrated in vacuo. The residue was purified by column chromatography and recrystalized from ethyl acetate/hexane (1:2) to give 500 mg (46% yield) of 5-(4-nitrobenzyl)amino-2-hydroxy ethylbenzoate as a yellow solid.: mp 106.5–107.5° C.

Elemental analysis for $C_{16}H_{16}N_2O_5$.

|  | % C | % H | % N |
|---|---|---|---|
| Calculated | 60.75 | 5.10 | 8.86 |
| Found | 60.68 | 5.24 | 9.04 |

SYNTHESIS EXAMPLE 9

Preparation of 5-(4-Nitrobenzyl)-N-acetylamino-2-hydroxy Ethylbenzoate

To a solution of 5-(4-nitrobenzyl)amino-2-hydroxy ethylbenzoate (500 mg, 1.58 mmole) in dried methanol (50 ml) was carefully added acetic anhydride (5 ml) at 0° C. under a nitrogen atmosphere. The reaction mixture was stirred for 2 hr at 10° C. After ice chips were slowly added to the reaction mixture, the solvent was removed in vacuo. The reaction mixture was extracted with ethyl acetate and $H_2O$, and the organic layer was washed with $H_2O$, 10% $NaHCO_3$ (30 ml×3) solution, 5% HCl (30 ml×2) solution and brine. The organic solution was dried over anhydrous $MgSO_4$ and evaporated. The residue was purified by column chromatography and recrystalized from ethyl acetateahexane (1:3) to give 400 mg (70% yield) of 5-(4-nitrobenzyl)-N-acetylamino-2-hydroxy ethylbenzoate as a pale yellow solid.: mp 105.5–106.0° C.

Elemental analysis for $C_{18}H_{18}N_2O_6$.

|  | % C | % H | % N |
|---|---|---|---|
| Calculated | 60.33 | 5.06 | 7.82 |
| Found | 60.54 | 5.35 | 8.12 |

SYNTHESIS EXAMPLE 10

Preparation of 5-(4-Nitrobenzyl)-N-acetylamino-2-acetoxy Ethylbenzoate

To a solution of 5-(4-nitrobenzyl)amino-2-hydroxy ethylbenzoate (500 mg, 1.58 mmole) in acetic anhydride (10 ml) was carefully added conc.$H_2SO_4$ (0.5 ml) at 0° C. under a nitrogen atmosphere. The reaction mixture was stirred for 30 min at 10° C. After ice chips were slowly added to the reaction mixture, the solvent was removed in vacuo. The reaction mixture was diluted with water and extracted with ethyl acetate. The organic layer was washed $H_2O$, 10% $NaHCO_3$ (30 ml×3) solution, 5% HCl (30 ml×2) solution and brine and then dried over anhydrous $MgSO_4$. After evaporation of the solvent, the residue was purified by column chromatography to give 450 mg (71% yield) of 5-(4-nitrobenzyl)-N-acetylamino-2-acetoxy ethylbenzoate as pale yellow oil.

Elemental analysis for $C_{20}H_{20}N_2O_7$.

|  | % C | % H | % N |
|---|---|---|---|
| Calculated | 60.00 | 5.03 | 7.00 |
| Found | 59.96 | 4.84 | 7.15 |

SYNTHESIS EXAMPLE 11

Preparation of 5-(4-Nitrobenzoyl)aminosalicylic Acid

By following the similar procedure in Synthesis Example 1 by using 5-aminosalicylic acid (500 mg, 3.26 mmole) and 4-nitrobenzoyl chloride (700 mg, 3.77 mmole), 550 mg (56% yield) of 5-(4-nitrobenzoyl)aminosalicylic acid was obtained as a pale yellow solid.: mp 270–271 ° C.

Elemental analysis for $C_{14}H_{10}N_2O_6$.

|  | % C | % H | % N |
|---|---|---|---|
| Calculated | 55.63 | 3.33 | 9.27 |
| Found | 55.82 | 3.43 | 9.08 |

SYNTHESIS EXAMPLE 12

Preparation of 5-(4-Nitrobenzenesulfonyl) aminosalicylic Acid

By following the similar procedure in Synthesis Example 1 by using 5-aminosalicylic acid (500 mg, 3.26 mmole) and 4-nitrobenzenesulsonyl chloride (720 mg, 3.26 mmole), 390 mg (35% yield) of 5-(4-nitrobenzenesulfonyl) aminosalicylic acid was obtained as a yellow solid.: mp 239–240 ° C.

Elemental analysis for $C_{13}H_{10}N_2O_7S$.

|  | % C | % H | % N | % S |
|---|---|---|---|---|
| Calculated | 46.15 | 2.98 | 8.28 | 9.48 |
| Found | 46.27 | 2.92 | 8.34 | 9.51 |

SYNTHESIS EXAMPLE 13

Preparation of 5-[2-(4-Nitrophenyl)ethyl] aminosalicylic Acid

By following the similar procedure in Synthesis Example 1 by using 5-aminosalicylic acid (500 mg, 3.26 mmole) and 4-nitrophenethyl bromide (900 mg, 3.92 mmole), 890 mg (50% yield) of 5-(4-nitrophenethyl)aminosalicylic acid was obtained as a pale yellow solid.: mp 234–236° C.

Elemental analysis for $C_{15}H_{14}N_2O_5$.

|  | % C | % H | % N |
|---|---|---|---|
| Calculated | 59.60 | 4.67 | 9.27 |
| Found | 59.77 | 4.79 | 9.24 |

SYNTHESIS EXAMPLE 14

Preparation of 5-[3-(4-Nitrophenyl)-n-propyl] aminosalicylic Acid

By following the similar procedure in Synthesis Example 1 by using 5-aminosalicylic acid (500 mg, 3.26 mmole) and 3-(4-nitrophenyl)propyl bromide (950 mg, 3.92 mmole), 520 mg (50% yield),of 5-[3-(4-nitrophenyl)-n-propyl] aminosalicylic acid was obtained as a pale yellow solid.: mp 229–231 ° C.

Elemental analysis for $C_{16}H_{16}N_2O_5$.

|  | % C | % H | % N |
|---|---|---|---|
| Calculated | 60.75 | 5.10 | 8.86 |
| Found | 60.77 | 5.07 | 8.89 |

EXPERIMENTAL EXAMPLE

Primary cortical cell cultures from embryonic mice were prepared and used to examine neuroprotective action of compounds. Mouse cortical cell culture system has been extensively used to study mechanisms and pharmacological intervention of neuronal death in neurological diseases. In brief, mouse cerebral cortices were removed from brains of the 15 day-old-fetal mice, in accordance with a protocol approved by our institutional animal care committee. The neocortices were gently triturated and plated on 24 well plates (5 hemispheres/plate) precoated with 100 $\mu$g/ml poly-D-lysine and 4 $\mu$g/ml laminine. Plating media consist of Eagles minimal essential media (MEM, Earles salts, supplied glutamine-free) supplemented with 5% horse serum, 5% fetal bovine serum, 2 mM glutamine, and 21 mM glucose. Cultures were maintained at 37° C. in a humidified 5% $CO_2$ atmosphere. After 7 days in vitro (DIV 7), cultures were shifted into a growth medium identical to the plating medium but lacking fetal serum. At DIV 7–9, 10 mM cytosine arabinofuranoside was included to halt overgrowth of glia. Mixed cultures of neurons and glia were then fed twice a week.

To induce neuronal injury by NMDA or $Zn^{2+}$, cortical cell cultures were exposed to toxic doses of NMDA for 10 min or $Zn^{2+}$ for 30 min in a HEPES-buffered control salt solution (HCSS): (in mM) 120 NaCl, 5KCl, 1.6 $MgCl_2$, 2.3 $CaCl_2$, 15 glucose, 20 HEPES and 10 NaOH. After exposure, cultures were washed out 3 times and exchanged with MEM adjusted to 25 mM glucose and 26.2 mM sodium bicarbonate, and placed in the $CO_2$ incubator for the next 20–24 hr. To induce free radical neurotoxicity, cortical cell cultures were continuously exposed to $Fe^{2+}$ or buthionine sulfoximine (BSO) for 20–24 hr, in MEM adjusted to 25 mM glucose and 26.2 mM sodium bicarbonate.

Overall cell injury was assessed microscopically under phase-contrast optics or by measuring amount of lactate dehydrogenase (LDH) released into the bathing medium 24 hr after neurotoxic insults as previously described (Koh and Choi, J Neurosci Methods 20:83–90, 1987). The percent neuronal death was normalized to the mean LDH value released 24 hr after continuous exposure 500 $\mu$M NMDA (=100) or a sham control (=0).

To examine anti-oxidant effect, DPPH (2,2-diphenyl-1-picryl-hydrazyl radical), a stable free radical, was dissolved in ethanol to make a 100 $\mu$M solution. A compound was reacted with DPPH or ethanol. After incubation for 30 min, relative decrease in DPPH absorption at 517 nm was measured by a spectrophotometer.

Experimental Example 1

Anti-oxidant Action of 5-Amino Salicylic Acid

Figure 1B:
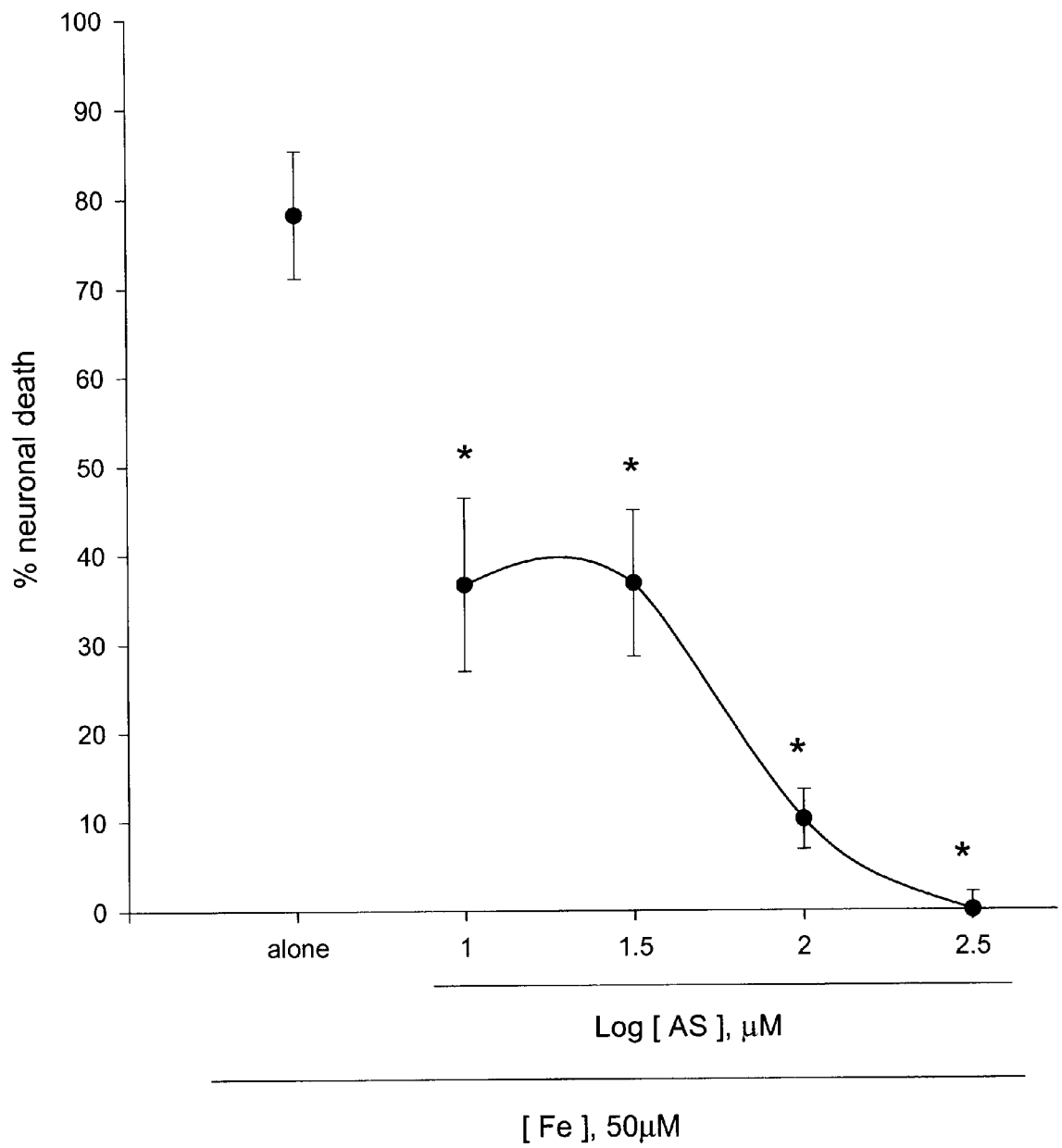
Figure 1C:
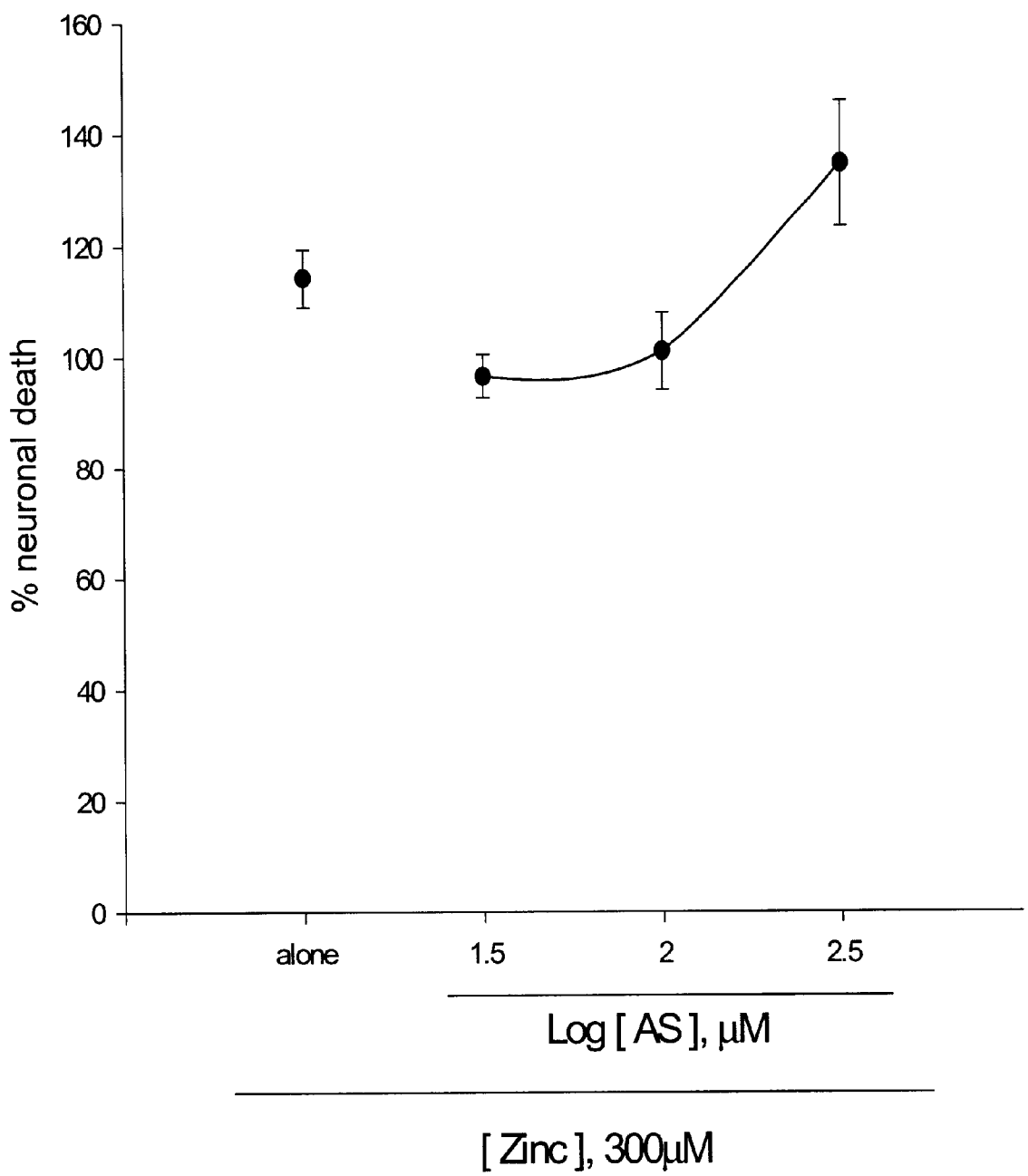
Figure 2A:
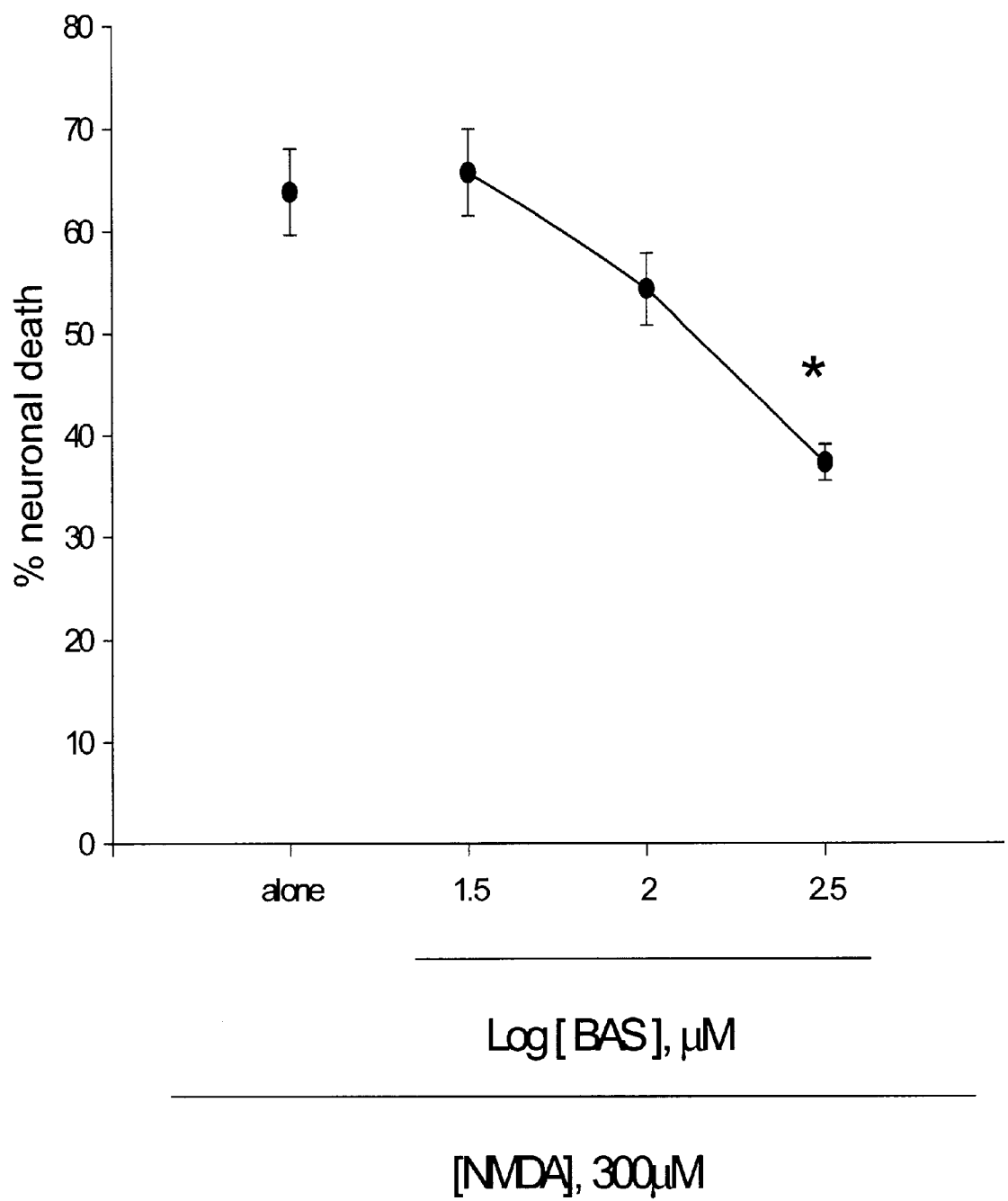
FIG. 2 is a result testing neuroprotective effects of 5-benzylamino salicylate (BAS) against neuronal death induced by NMDA (2a), Fe2+ (2b), buthionine sulfoximine (BSO) (2c) or Zn2+ (2d) in cultured cortical cells.
Figure 2B:
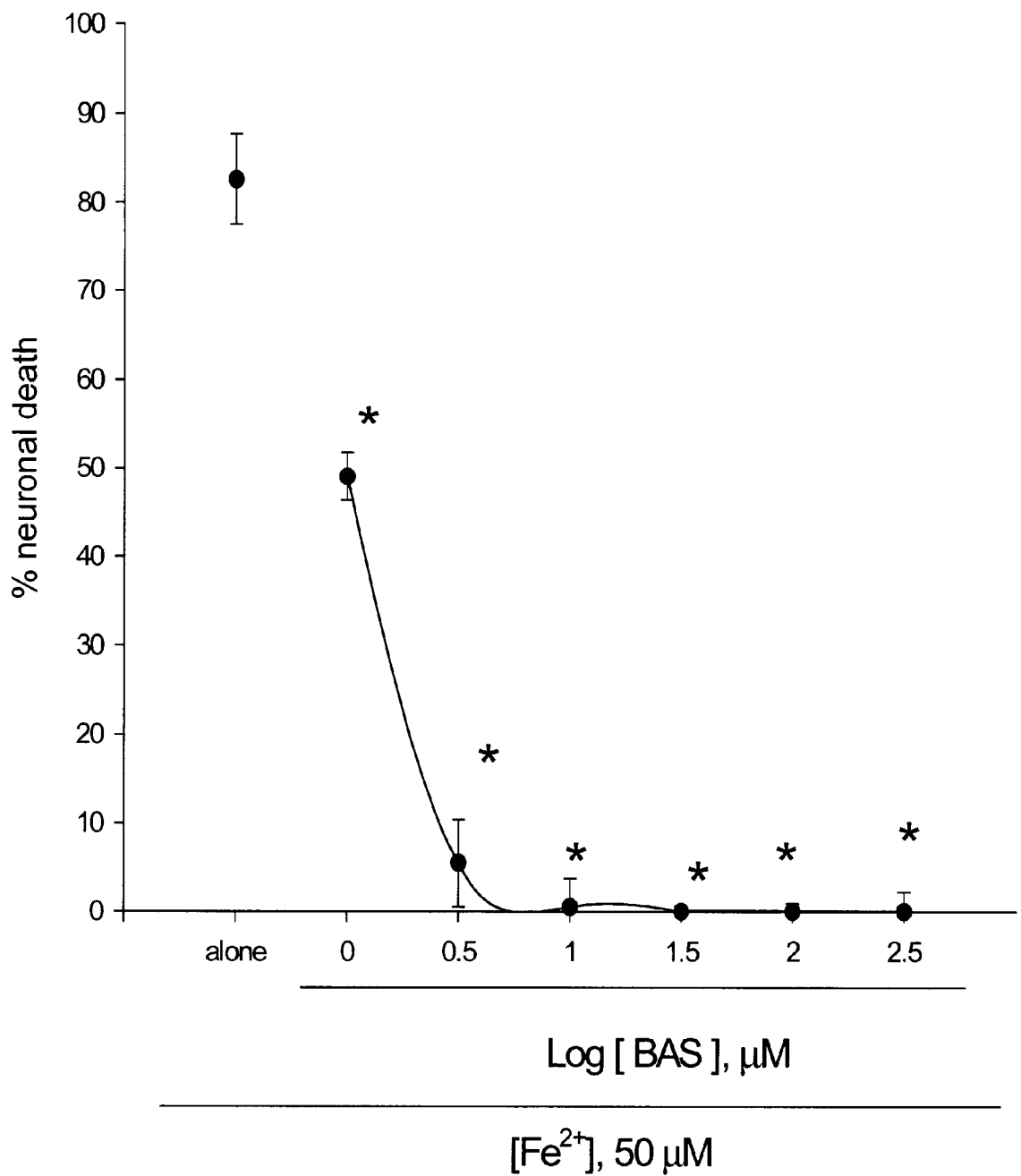
Figure 2C:
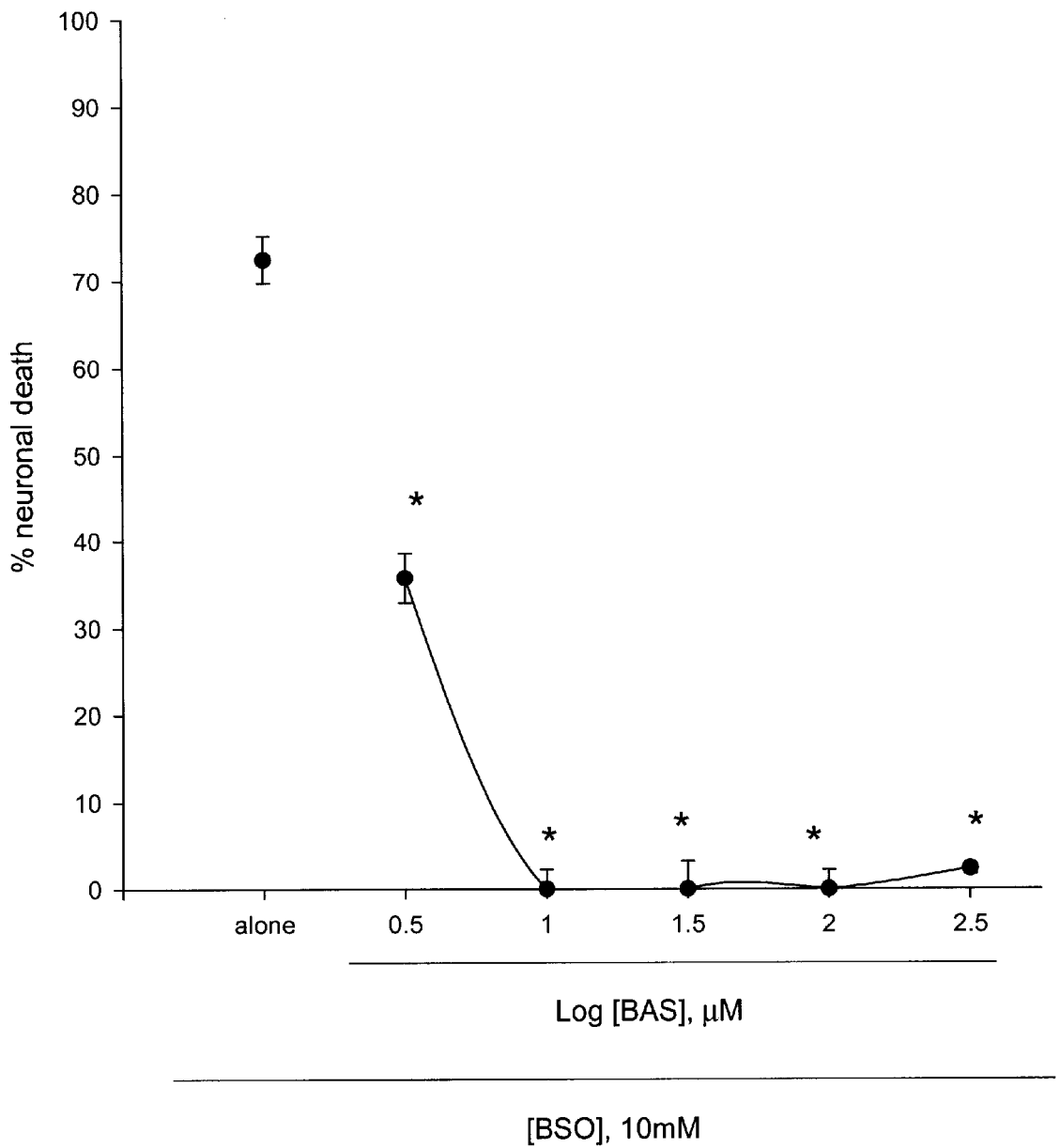
Figure 2D:
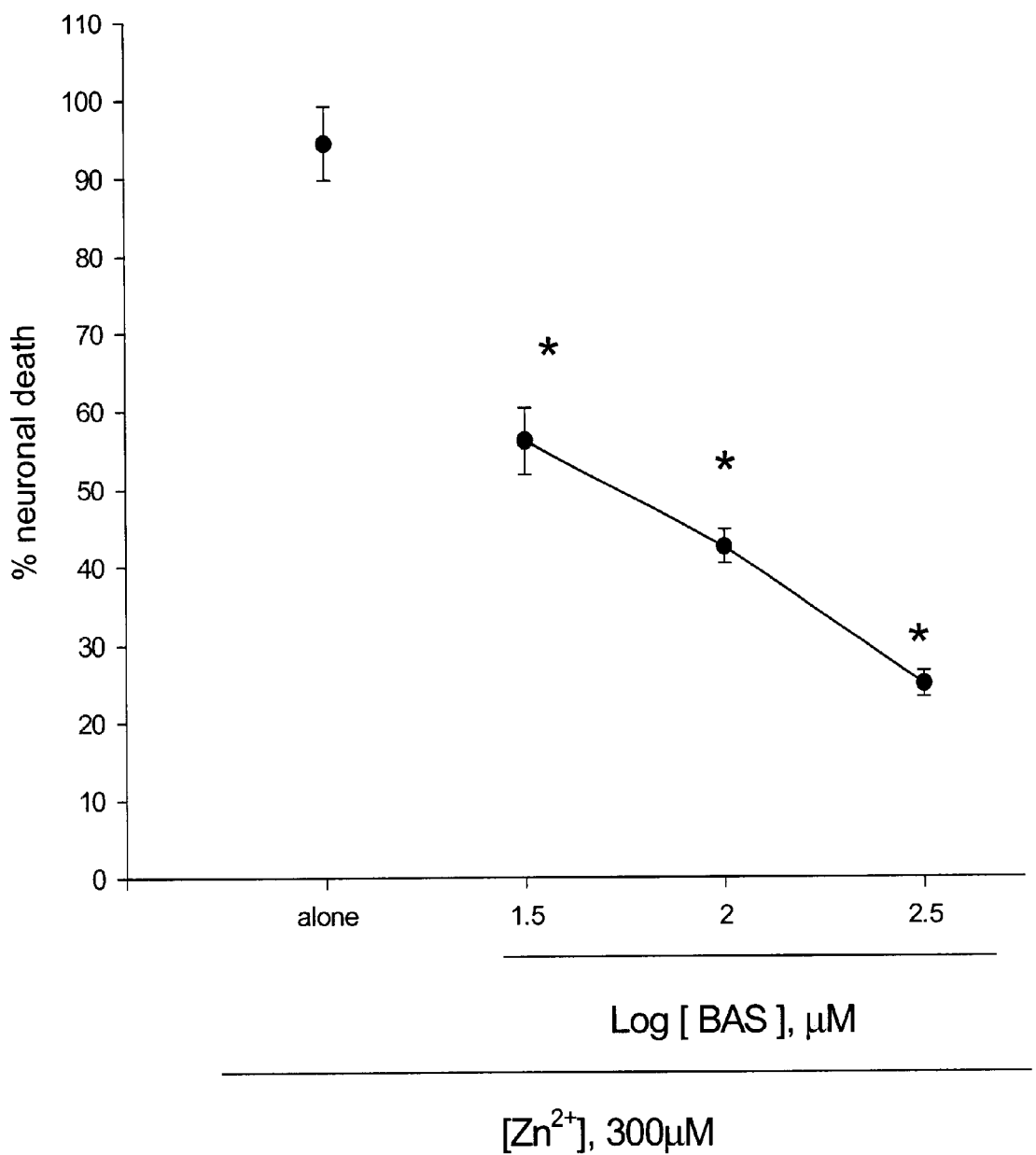

The neuroprotective action of 5-amino salicylic acid (AS) was examined in primary cortical cell cultures. Mouse cortical cell cultures (DIV 12–14) were exposed to 300 $\mu$M NMDA for 10 min (1a), continuously to 50 $\mu$M $Fe^{2+}$ (1b), or 300 $\mu$M $Zn^{2+}$ for 30 min (1c), alone or with inclusion of 10–300 µM 5-amino salicylic acid (AS). Neuronal death was analyzed 24 hr later by measuring levels of LDH released into the bathing medium, mean±SEM (n=9–12 (1a), n=4–8 (1b) or n=4 (1c) culture wells per condition), scaled to mean LDH efflux value 24 hr after sham wash (=0) and continuous exposure to 500 µM NMDA (=100). The result as shown in FIG. 1 indicates significant difference from relevant control at p<0.05 using ANOVA and Student-Neuman-Keuls' test. Inclusion of 10–300 µM AS did not attenuate neuronal death evolving 24 hr after 10 min-exposure to 300 µM NMDA (FIG. 1a). Interestingly, addition of 10–100 µM AS dose-dependently prevented free radical neurotoxicity following 24 hr-exposure to $Fe^{2+}$ (FIG. 1b). Neuronal death 24 hr after 30 min-exposure to 300 µM $Zn^{2+}$ was not reduced by continuous inclusion of AS during and post $Zn^{2+}$ treatment (FIG. 1c). The neuroprotective action of AS against free radical neurotoxicity was attributable to direct anti-oxidant property of the compound as AS decreased levels of DPPH, a stable free radical (Table 1). Compared to trolox, a membrane-permeable form of vitamin E, AS was a weak anti-oxidant.

cultures (DIV 12–14) were exposed to 300 µM NMDA for 10 min (2a), continuously to 50 µM $Fe^{2+}$ (2b) or 10 mM BSO (2c), or 300 µM $Zn^{2+}$ for 30 min (2d), alone or with inclusion of indicated doses of 5-benzylamino salicylate (BAS). Neuronal death was analyzed 24 hr later by measuring levels of LDH released into the medium, mean±SEM (n=7–8 (2a), n=3–6 (2b), n=4 (2c), or n=4 (2d) culture wells per condition). FIG. 2 indicates significant difference from relevant control, at p<0.05 using ANOVA and Student-Neuman-Keuls test. Concurrent addition of 300 µM 5-benzylaminosalicylic acid (BAS) reduced NMDA-induced neuronal death approximately by 50% (FIG. 2a). Neuronal death following exposure to 50 µM $Fe^{2+}$ (FIG. 2b) or 10 mM BSO (FIG. 2c) was substantially reduced in the presence of 1 µM BAS and near completely blocked by addition of 3 µM BAS. Administration of 30–300 µM BAS dose-dependently reduced neuronal death 24 hr following exposure to 300 µM $Zn^{2+}$ for 30 min (FIG. 2d). Like AS or

TABLE 1

Anti-oxidant property of AS

| | Reactants | Concentrations of Trolox or AS (µM) | | | | | |
|---|---|---|---|---|---|---|---|
| | | 0 | 3 | 10 | 30 | 100 | 300 |
| $A_{517nm}$ | DPPH alone | 1.2 ± 0.05 | | | | | |
| | DPPH + Trolox | | 1.08 ± 0.1 | 0.89 ± 0.08* | 0.39 ± 0.06* | 0.05 ± 0.01* | 0.03 ± 0.01* |
| | DPPH + AS | | — | 1.03 ± 0.05 | 0.9 ± 0.06* | 0.45 ± 0.07* | 0.16 ± 0.00* |

AS or trolox was reacted with 100 uM DPPH dissolved in ethanol for 30 min. Anti-oxidant property was analyzed by measuring changes in the level of DPPH at 517 nm, trolox, BAS acted as a direct anti-oxidant (Table 2). The anti-oxidant property of BAS was observed at a dose as low as 1 µM.

TABLE 2

Anti-oxidant property of BAS

| | [BAS], µM | | | | | | |
|---|---|---|---|---|---|---|---|
| | 0 | 1 | 3 | 10 | 30 | 100 | 300 |
| $A_{517nm}$ | 1.2 ± 0.05 | 1.07 ± 0.07 | 1.01 ± 0.07 | 0.71 ± 0.09* | 0.21 ± 0.04* | 0.15 ± 0.02* | 0.16 ± 0.01* | mean±SEM (n=3 test tubes per condition), after subtracting background value resulting from ethanol alone. FIG. 1 indicates significant difference from DPPH alone at P<0.05, using ANOVA and Student-Neuman-Keuls test.

AS can protect neurons from free radical injuries without beneficial effects against NMDA or $Zn^{2+}$ neurotoxicity. However, AS is weaker than trolox in scavenging free radicals.

Experimental Example 2

Neuroprotective Effects of 5-Benzylaminosalicylic Acid and its Derivatives

1. Neuroprotective Effects of 5-Benzylaminosalicylic Acid

BAS was synthesized and examined against neuronal injuries induced in cortical cell cultures. Mouse cortical cell BAS was reacted with 100 µM DPPH dissolved in ethanol for 30 min. Anti-oxidant property was analyzed by measuring changes in DPPH at 517 nm, mean±SEM (n=3 test tubes per condition), after subtracting background value resulting from ethanol alone. FIG. 1 indicates significant difference from DPPH alone ([BAS]=O) at P<0.05, using ANOVA and Student-Neuman-Keuls test.

2. BAS Derivatives

Figure 3A:
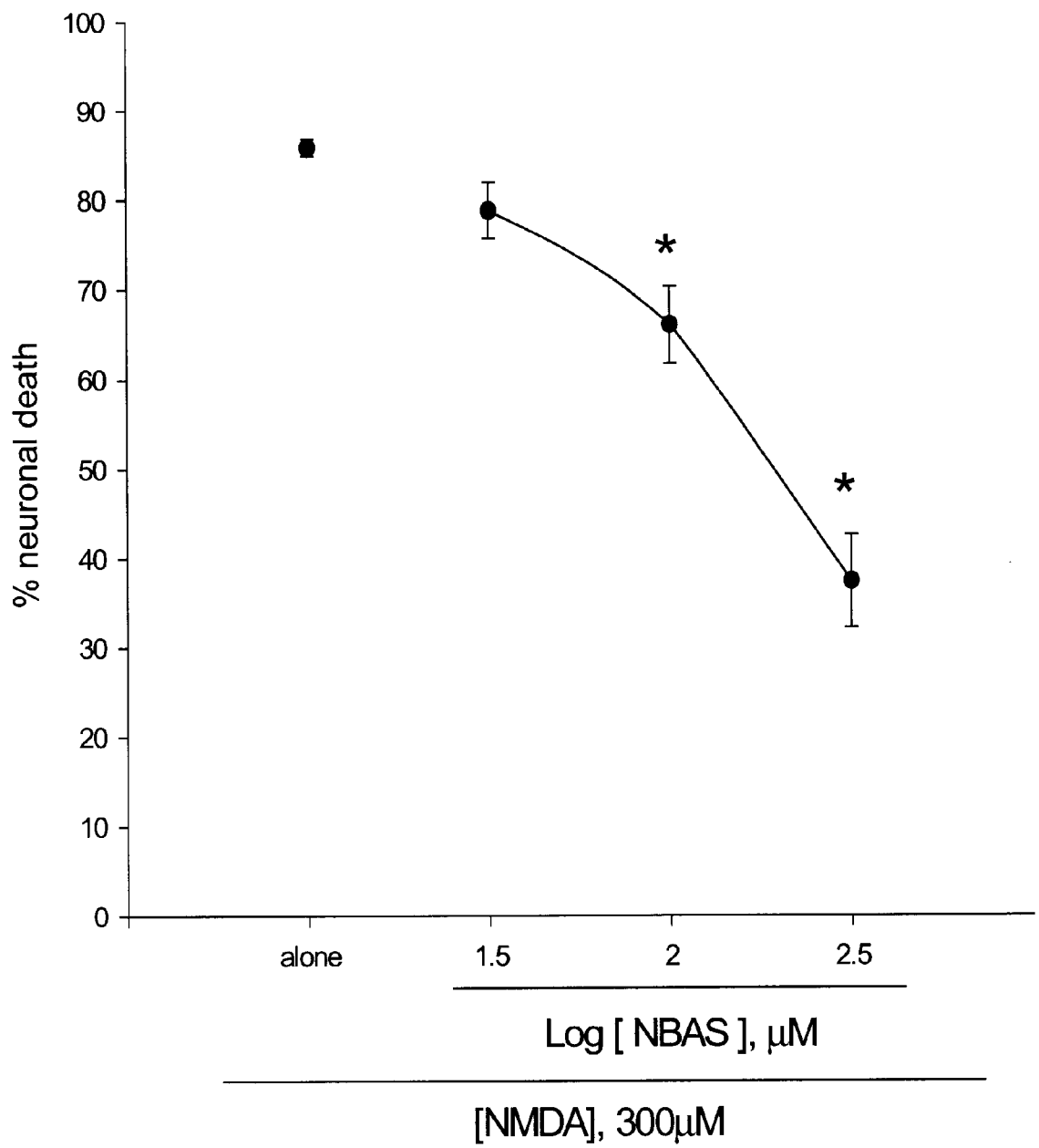
FIG. 3 is a result testing neuroprotective effects of 5-(4-nitrobenzyl)aminosalicylic acid (NBAS) against neuronal death induced by NMDA (3a), Fe2+ (3b) or Zn2+ (3c) in cultured cortical cells.
Figure 3B:
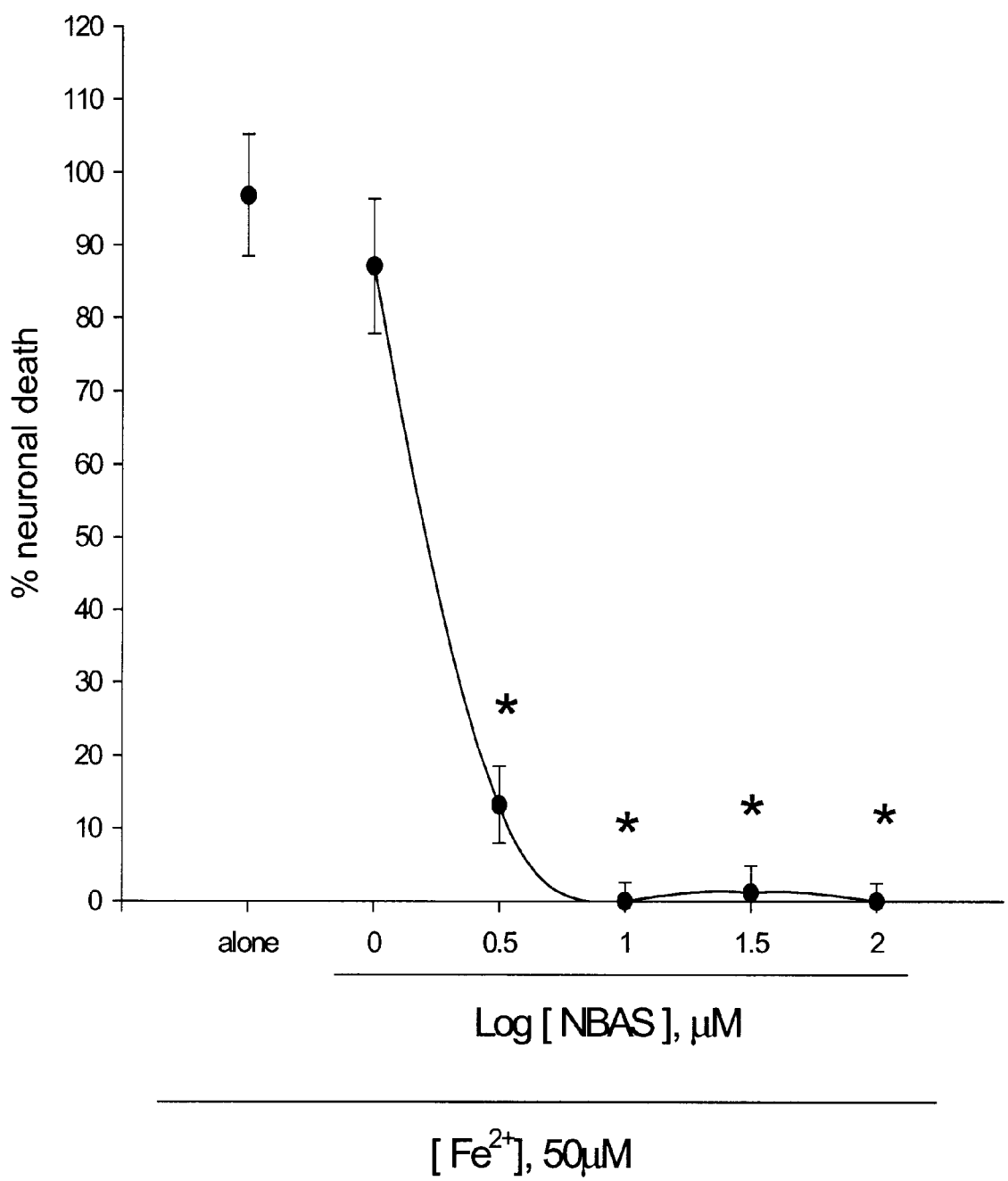
Figure 3C:
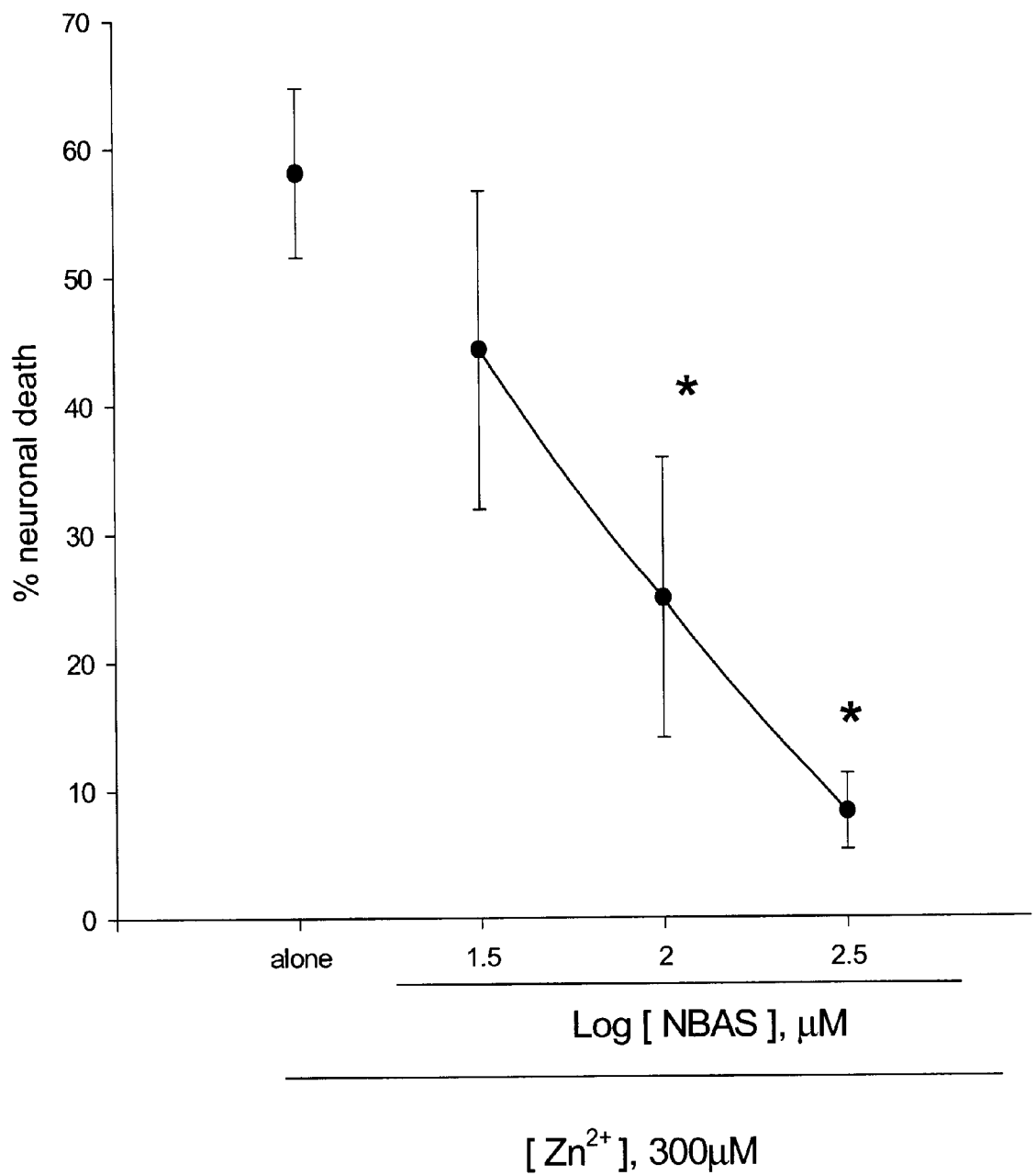

BAS derivatives were synthesized by substituting —H at para position of benzylamino group with —$NO_2$ [5-(4-nitrobenzylamino)salicylic acid, NBAS], —Cl [5-(4-chlorobenzylamino)salicylic acid, CBAS], —$CF_3$ [5-(4-trifluoromethylbenzylamino)salicylic acid, TBAS]. Mouse cortical cell cultures (DIV 12–14) were exposed to 300 µM NMDA for 10 min (3a), continuously to 50 µM $Fe^{2+}$ (3b), or 300 µM $Zn^{2+}$ for 30 min (3c), alone or with inclusion of indicated doses of 5-(4-nitrobenzyl)aminosalicylic acid (NBAS). Neuronal death was analyzed 24 hr later by measuring levels of LDH released into the medium, mean±SEM (n=7–8 (3a), n=3–6 (3b), or n=4 (3c) culture wells per condition). The result as shown in FIG. 3 indicates significant difference from relevant control, at p<0.05 using ANOVA and Student-Neuman-Keuls test.

Figure 4A:
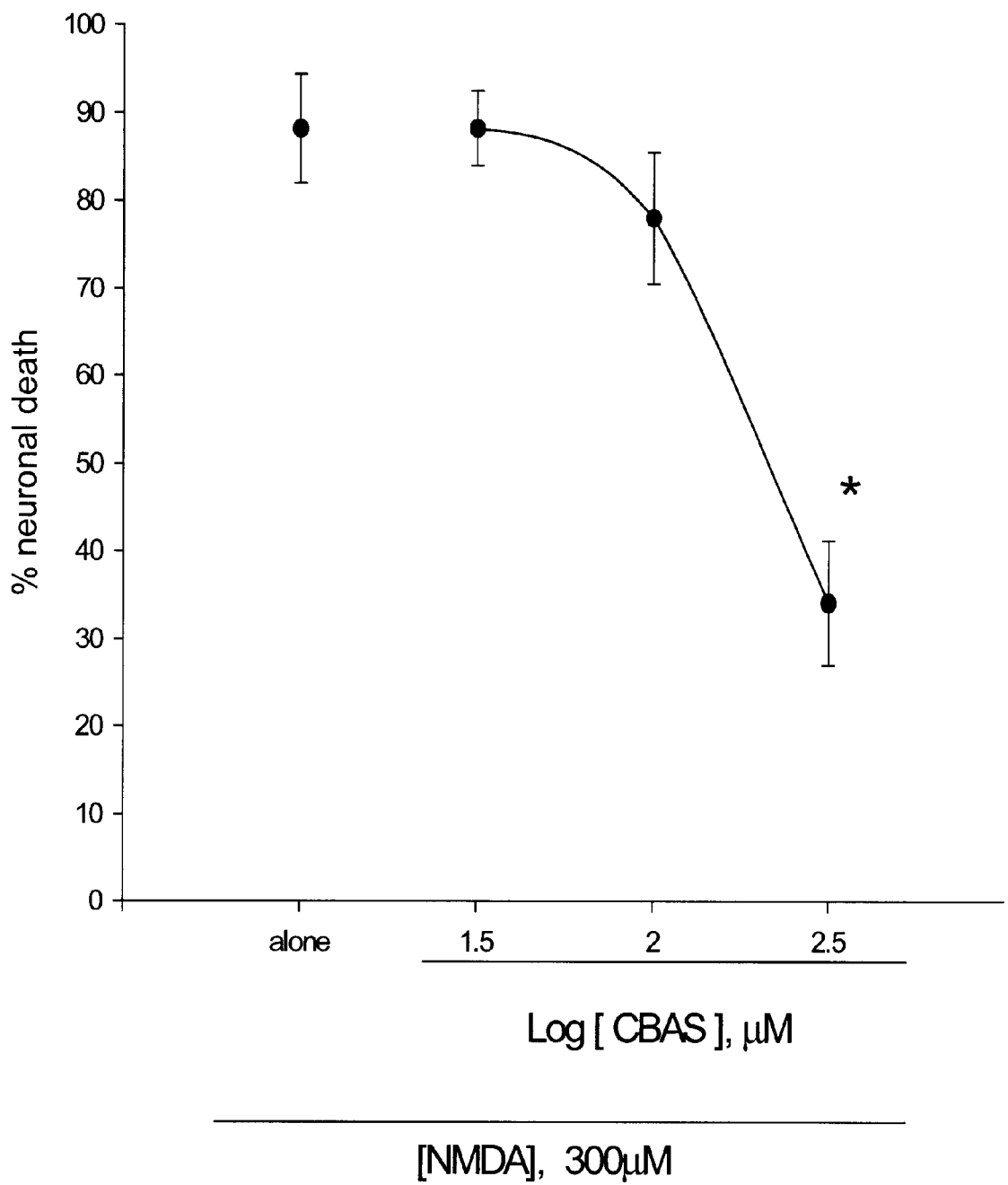
FIG. 4 is a result testing neuroprotective effects of 5-(4-chlorobenzyl)aminosalicylic acid (CBAS) against neuronal death induced by NMDA (4a), Fe2+ (4b) or Zn2+ (4c) in cultured cortical cells.
Figure 4B:
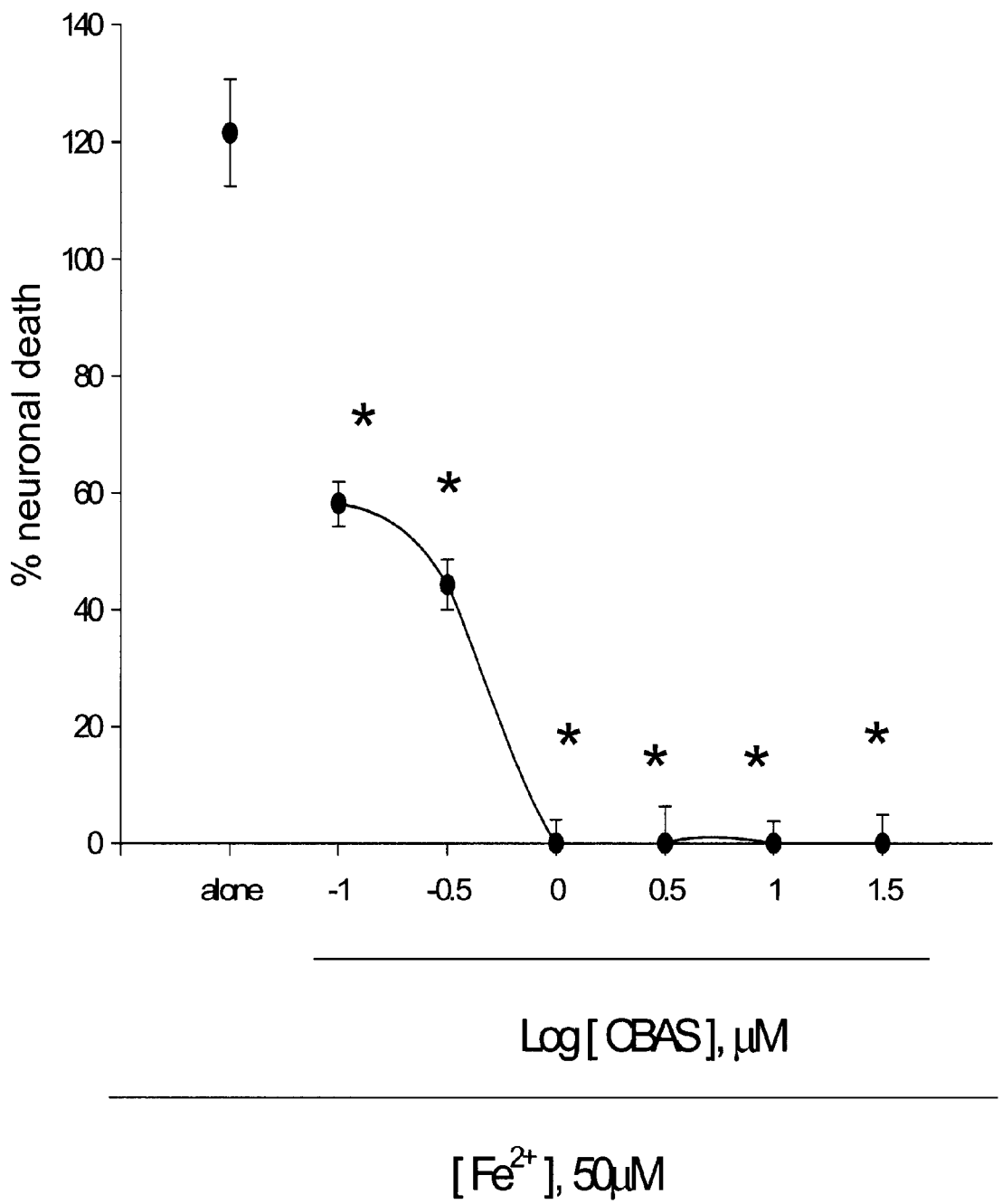
Figure 4C:
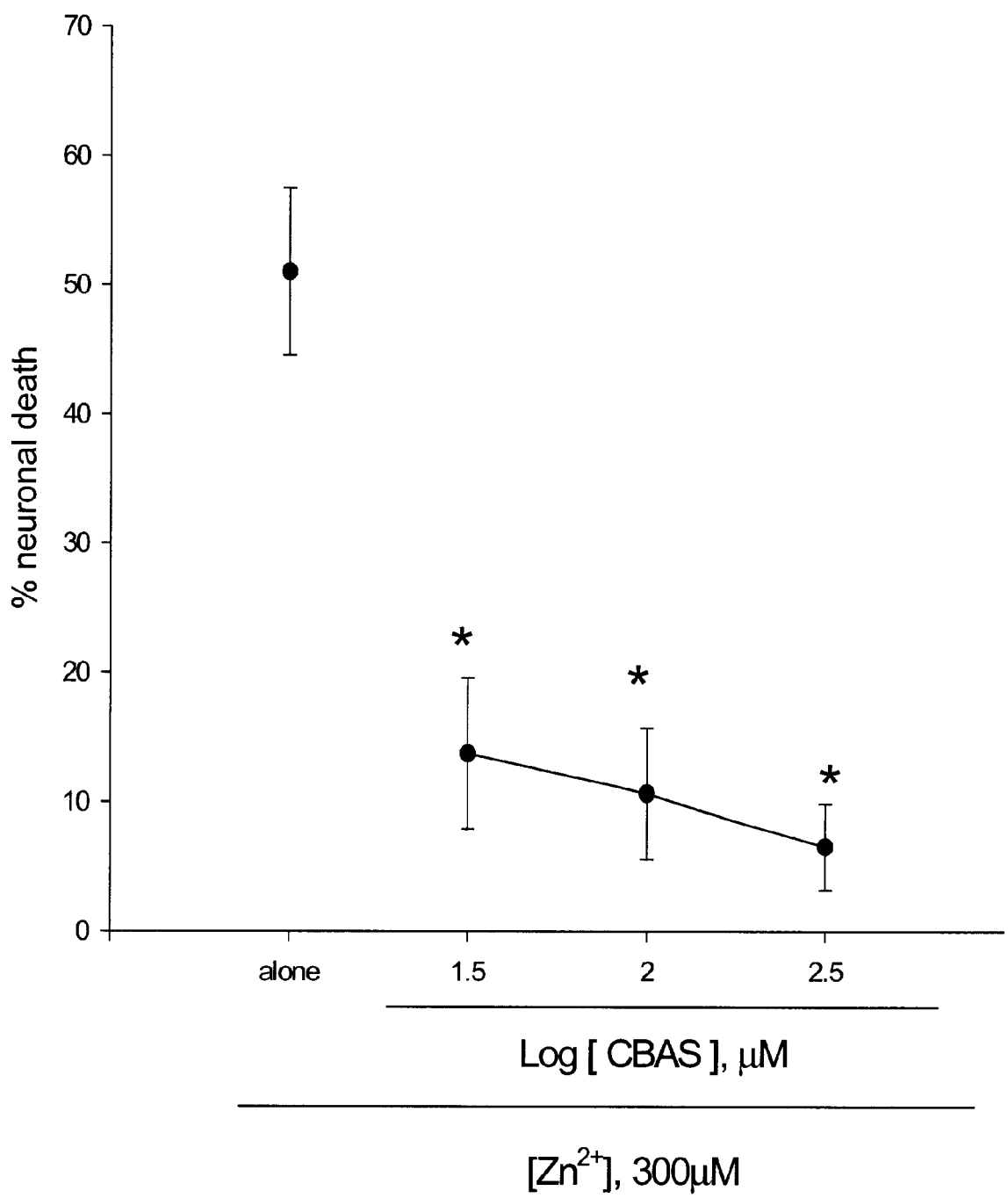

Mouse cortical cell cultures (DIV 12–14) were exposed to 300 $\mu$M NMDA for 10 min (4a), continuously to 50 $\mu$M $Fe^{2+}$ (4b), or 300 $\mu$M $Zn^{2+}$ for 30 min (4c), alone or with inclusion of indicated doses of 5-(4-chlorobenzyl)aminosalicylic acid (CBAS). Neuronal death was analyzed 24 hr later by measuring levels of LDH released into the medium, mean±SEM (n=3–4 (4a), n=3–12 (4b), or n=4 (4c) culture wells per condition). The result as shown in FIG. 4 indicates significant difference from relevant control, at p<0.05 using ANOVA and Student-Neuman-Keuls test.

Mouse cortical cell cultures (DIV 12–14) were exposed to 300 $\mu$M NMDA for 10 min (5a), continuously to 50 $\mu$M $Fe^{2+}$ (5b), or 300 $\mu$M $Zn^{2+}$ for 30 min (5c), alone or with inclusion of indicated doses of 5-(4-Trifluoromethylbenzyl) aminosalicylic acid (TBAS). Neuronal death was analyzed 24 hr later by measuring levels of LDH released into the medium, mean±SEM (n=3–4 (5a), n=3–11 (5b), or n=4 (5c) culture wells per condition). The result as shown in FIG. 5 indicates significant difference from relevant control, at p<0.05 using ANOVA and Student-Neuman-Keuls test.

Figure 6A:
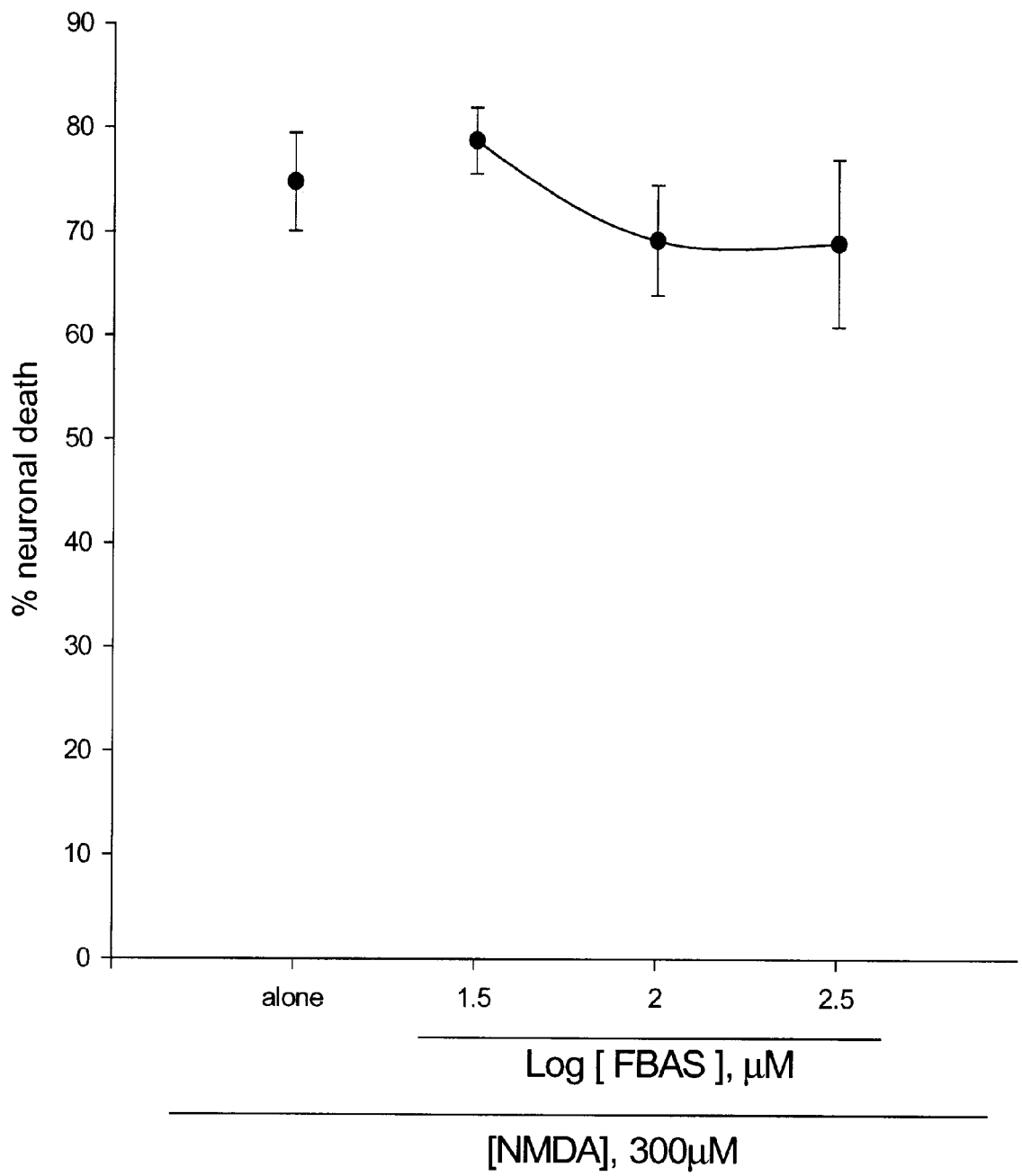
FIG. 6 is a result testing neuroprotective effects of 5-(4-Fluorobenzyl)aminosalicylic acid (FBAS) against neuronal death induced by NMDA (6a) or Fe2+ (6b) in cultured cortical cells.
Figure 6B:
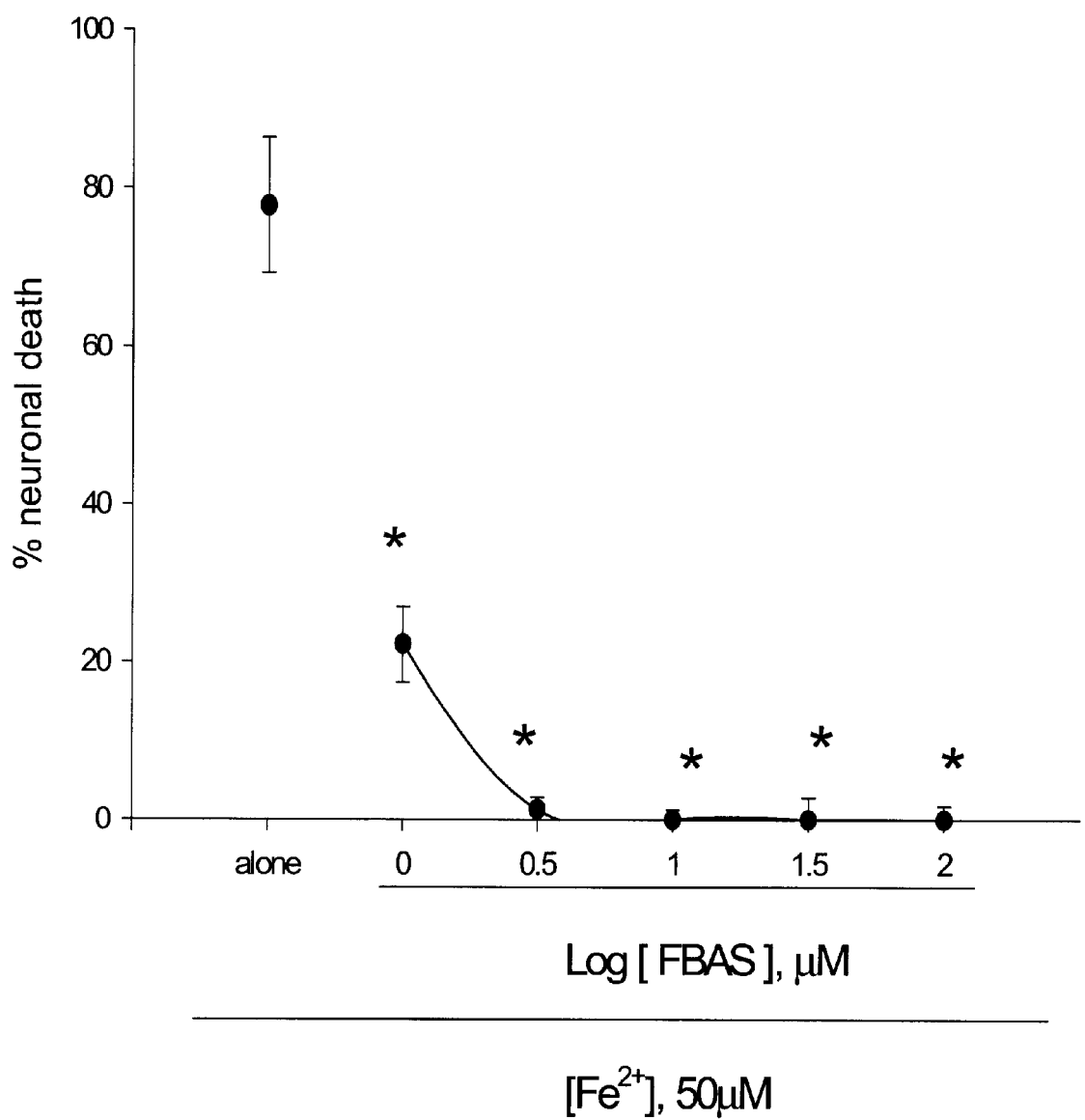

Mouse cortical cell cultures (DIV 12–14) were exposed to 300 $\mu$M NMDA for 10 min (6a) or continuously to 50 $\mu$M $Fe^{2+}$ (6b) alone or with inclusion of indicated doses of 5-(4-Fluorobenzyl)aminosalicylic acid(FBAS). Neuronal death was analyzed 24 hr later by measuring levels of LDH released into the medium, mean±SEM (n=7–8 (6a) or n=4–8 (6b) culture wells per condition). The result as shown in FIG. 6 indicates significant difference from relevant control, at p<0.05 using ANOVA and Student-Neuman-Keuls test.

Figure 7A:
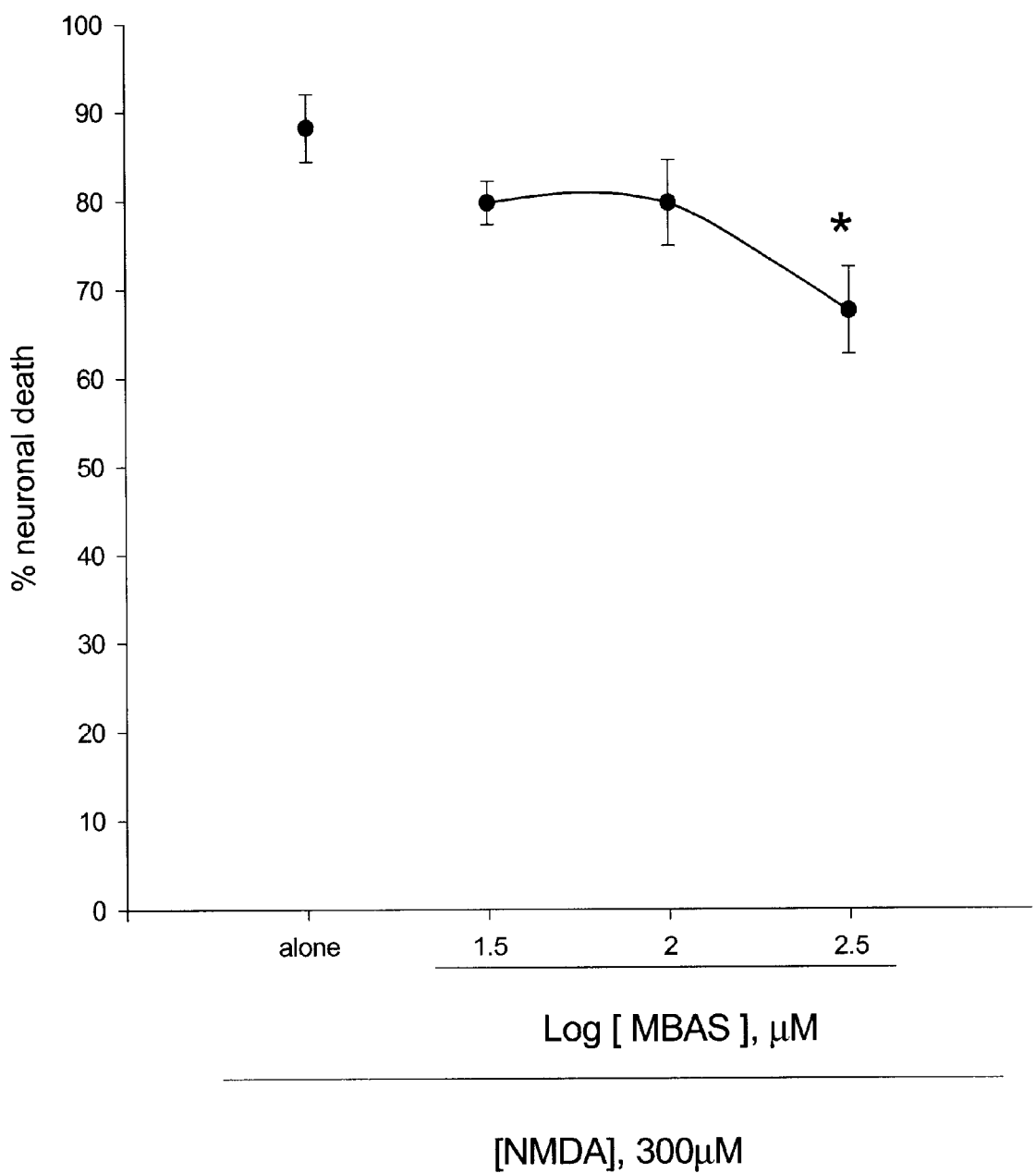
FIG. 7 is a result testing neuroprotective effects of 5-(4-methoxybenzyl)aminosalicylic acid(MBAS) against neuronal death induced by NMDA (7a) or Fe2+ (7b) in cultured cortical cells.
Figure 7B:
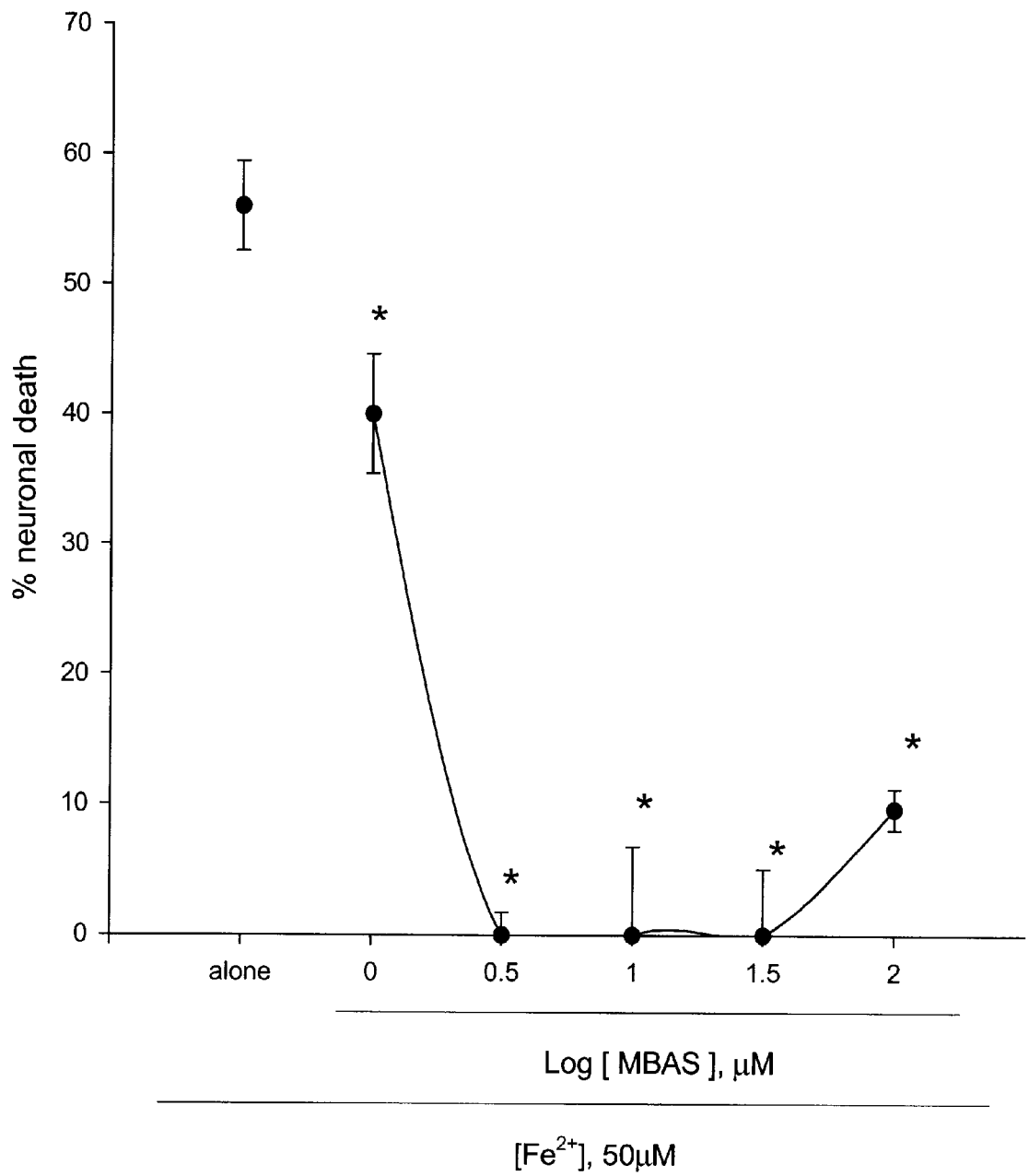

Mouse cortical cell cultures (DIV 12–14) were exposed to 300 $\mu$M NMDA for 10 min (7a) or continuously to 50 $\mu$M $Fe^{2+}$ (7b) alone or with inclusion of indicated doses of 5-(4-methoxybenzyl)aminosalicylic acid (MBAS). Neuronal death was analyzed 24 hr later by measuring levels of LDH released into the medium, mean±SEM (n=7–8 (7a) or n=4–8 (7b) culture wells per condition). The result as shown in FIG. 7 indicates significant difference from relevant control, at p<0.05 using ANOVA and Student-Neuman-Keuls test.

Figure 5A:
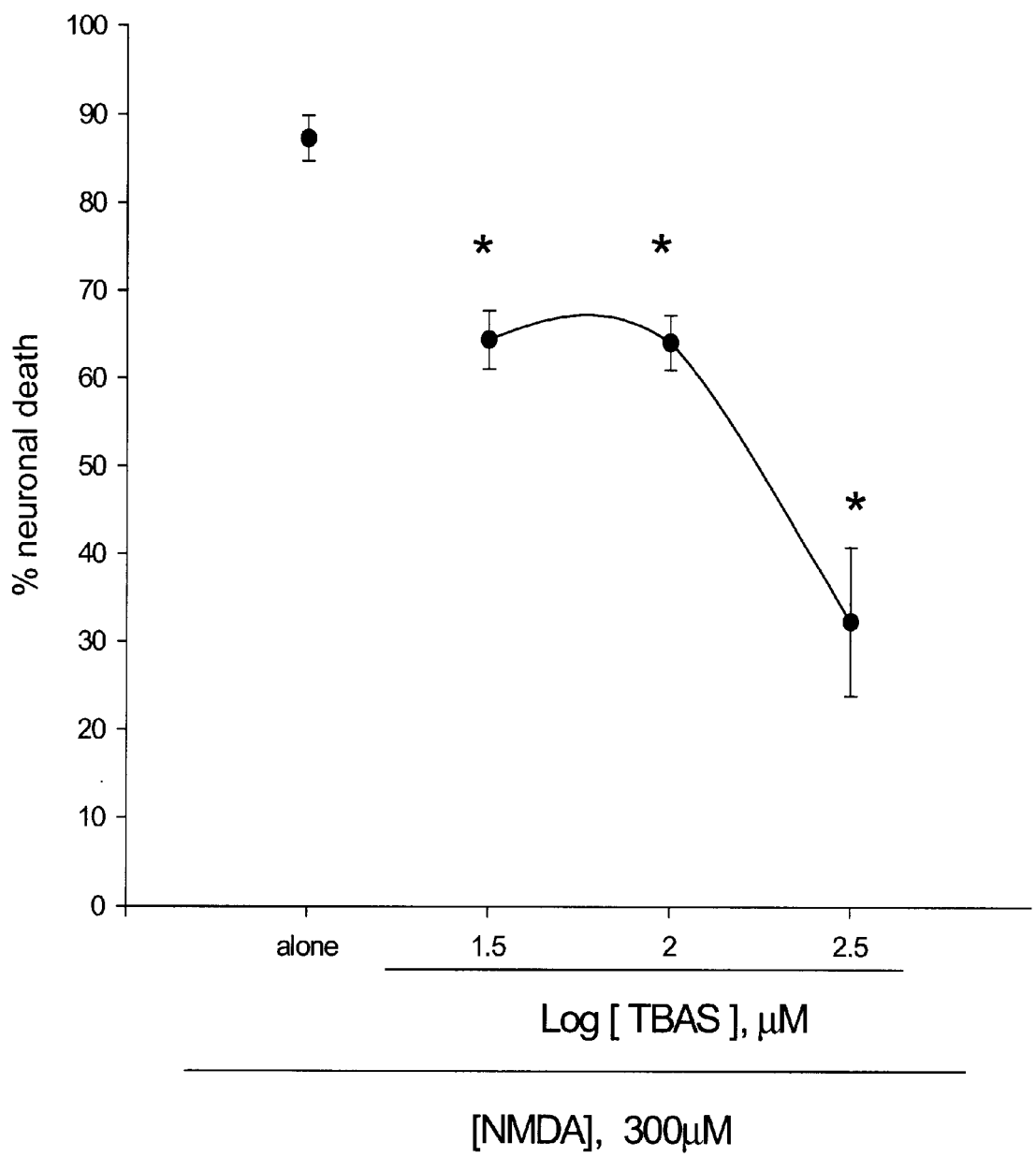
FIG. 5 is a result testing neuroprotective effects of 5-(4-Trifluoromethylbenzyl)aminosalicylic acid (TBAS) against neuronal death mediated by NMDA (5a), Fe2+ (5b) or Zn2+ (5c) in cultured cortical cells.
Figure 5B:
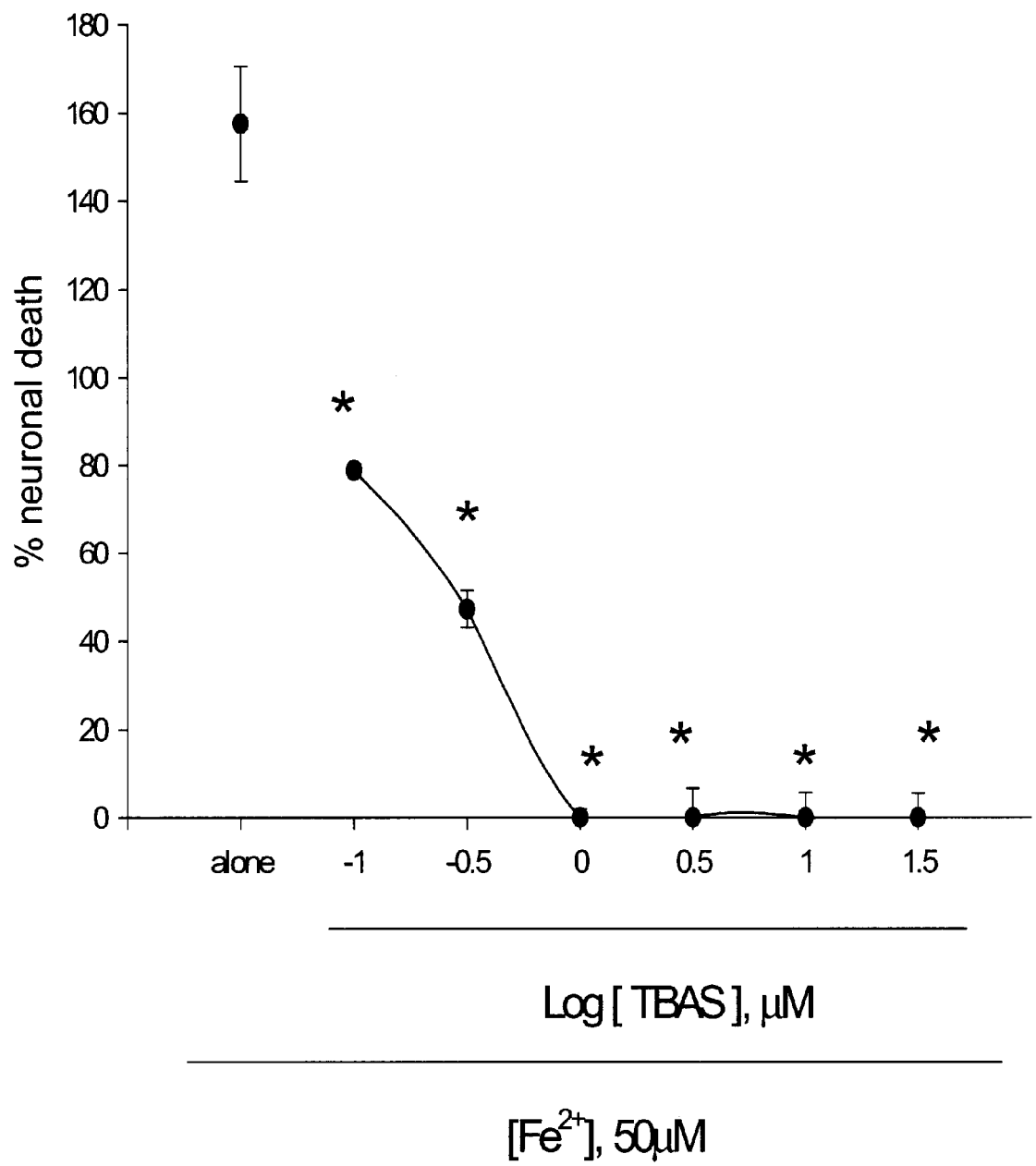
Figure 5C:
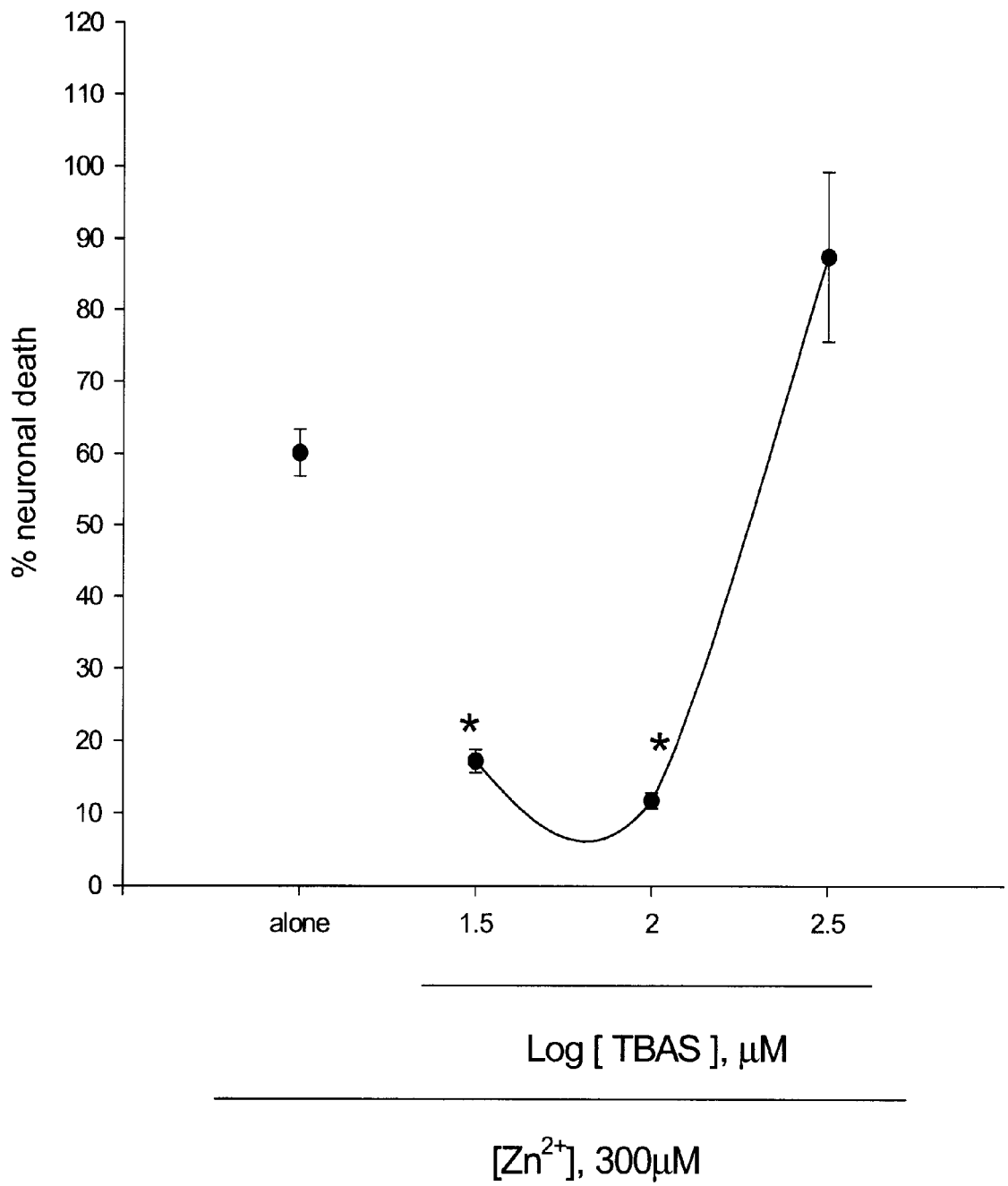

This substitution with electron-withdrawing group did not reduce neuroprotective effects of BAS against NMDA, $Zn^{2+}$, or free radical neurotoxicity (FIGS. 3–5). These BAS derivatives were more potent than BAS in preventing free radical neurotoxicity.

TABLE 3

Anti-oxidant property of NBAS

| | [NBAS], $\mu$M | | | | |
|---|---|---|---|---|---|
| | 0 | 10 | 30 | 100 | 300 |
| $A_{517nm}$ | 1.21 ± 0.01 | 0.37 ± 0.1* | 0.04 ± 0.01* | 0.04 ± 0.00* | 0.04 ± 0.00* |

NBAS was reacted with 100 uM DPPH dissolved in ethanol for 30 min. Anti-oxidant property was analyzed by measuring changes in DPPH at 517 nm, mean±SEM (n=3 test tubes per condition), after subtracting background value resulting from ethanol alone. Table 3 indicates significant difference from DPPH alone ([reactant]=O) at P<0.05, using ANOVA and Student-Neuman-Keuls test.

Substituting —$NO_2$ with —F or —$OCH_3$ resulted in decreased neuroprotection against NMDA toxicity but appeared to increase neuroprotective potential against free radical injury (FIGS. 6 and 7).

Experimental Example 3

Figure 8A:
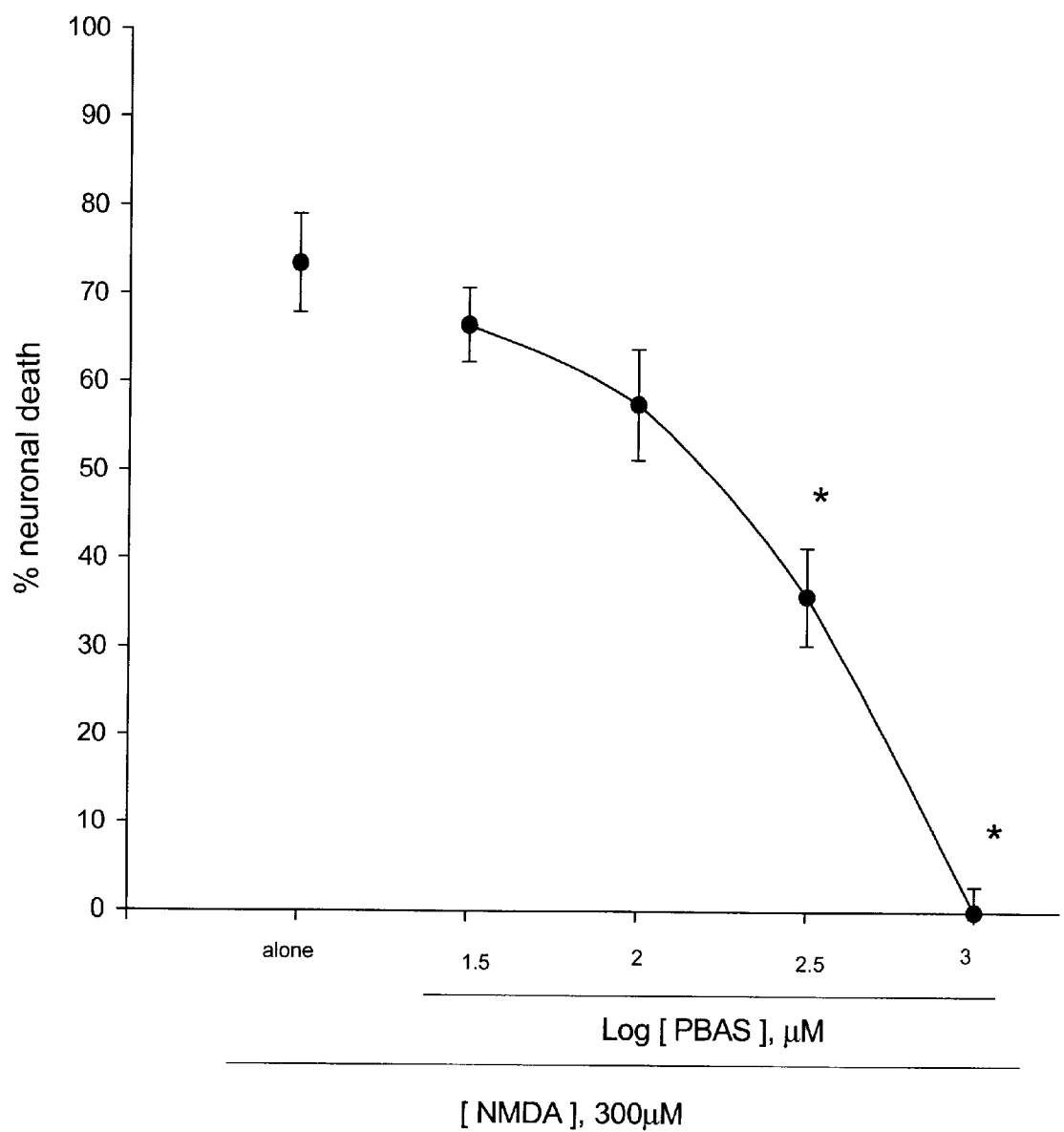
FIG. 8 is a result testing neuroprotective effects of 5-(pentafluorobenzyl)amino salicylic acid (PBAS) against neuronal death induced by NMDA (8a), Fe2+ (8b), BSO (8c) or Zn2+ (8d) in cultured cortical cells.
Figure 8B:
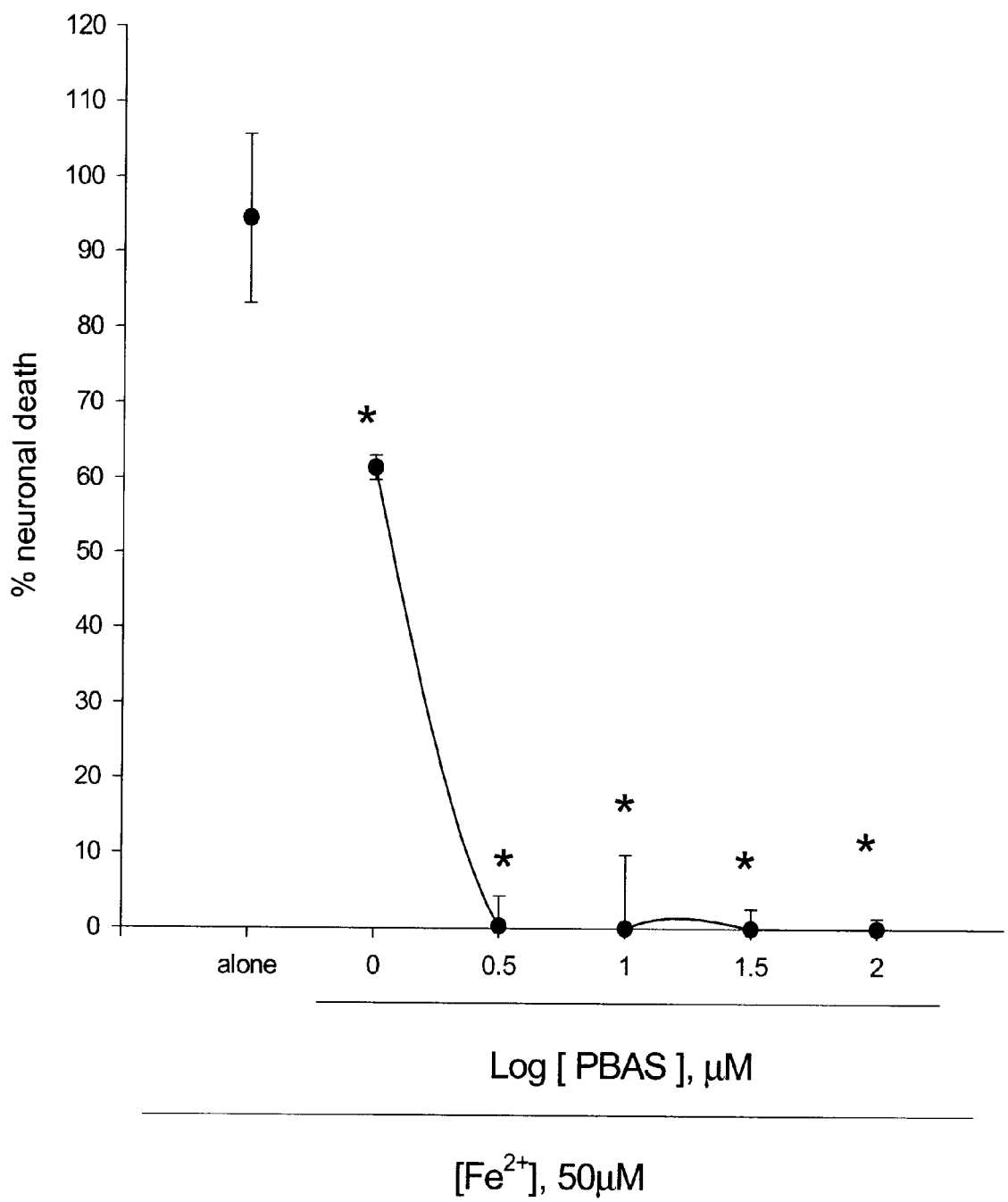
Figure 8C:
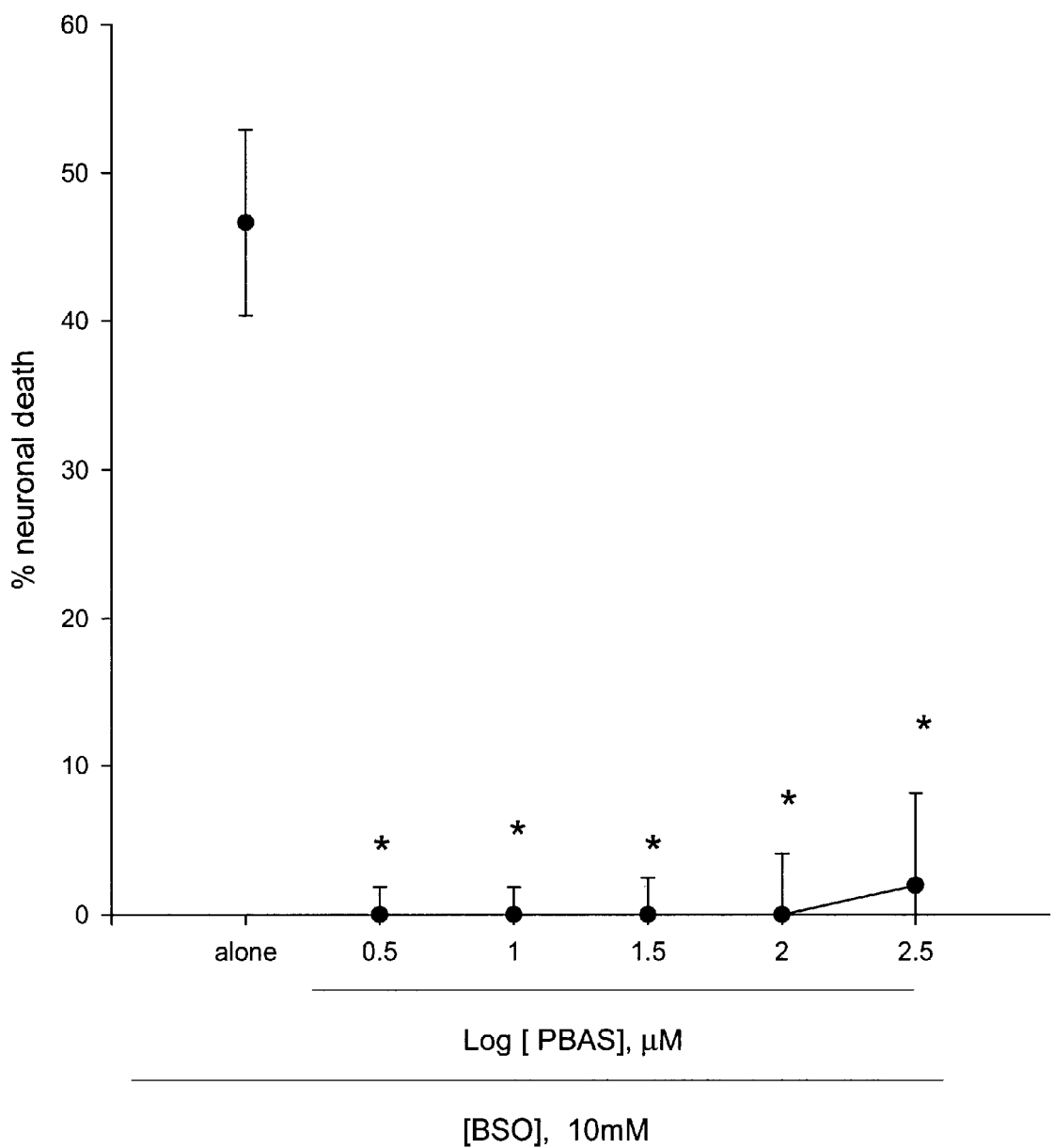
Figure 8D:
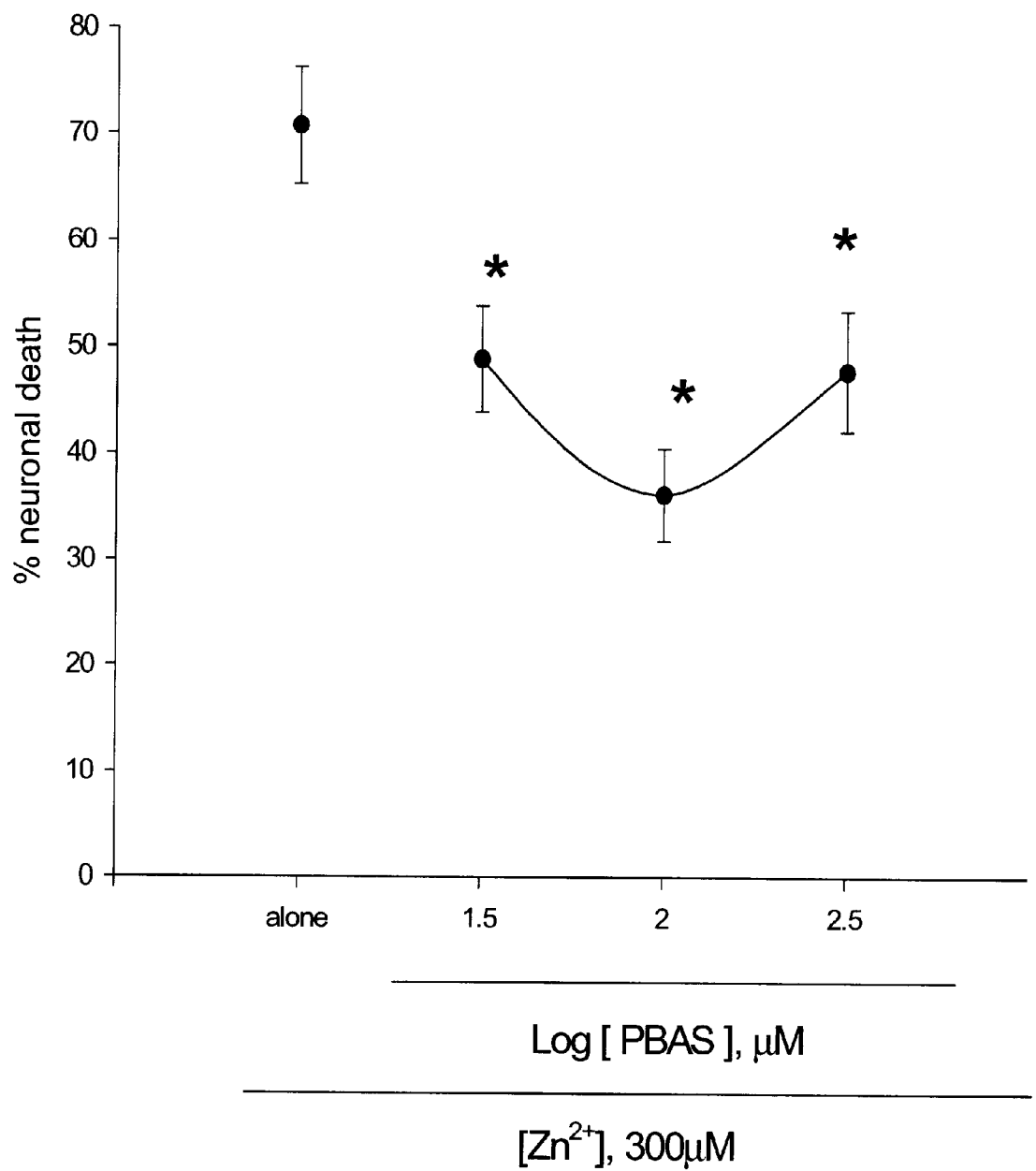

Neuroprotective Effects of 5-(Pentafluorobenzyl) amino Salicylic Acid 5-(pentafluorobenzyl)amino salicylic acid (PBAS) was synthesized and tested against neuronal injuries. Mouse cortical cell cultures (DIV 12–14) were exposed to 300 $\mu$M NMDA for 10 min (8a), continuously to 50 $\mu$M $Fe^{2+}$ (8b) or 10 mM BSO (8c), or 300 $\mu$M $Zn^{2+}$ for 30 min (8d), alone or with inclusion of indicated doses of 5-(pentafluorobenzyl) amino salicylic acid (PBAS). Neuronal death was analyzed 24 hr later by measuring levels of LDH released into the medium, mean±SEM (n=11–16 (8a), n=3–6 (8b), n=4–11 (8c), or n=12 (8d) culture wells per condition). The result as shown in FIG. 8 indicates significant difference from relevant control, at p<0.05 using ANOVA and Student-Neuman-Keuls test. Concurrent addition of 100–1000 $\mu$M PBAS reduced NMDA-induced neuronal death in a dose-dependent manner. Treatment with 300 $\mu$M PBAS reduced NMDA neurotoxicity approximately by 65% (FIG. 8a). Increasing doses of PBAS up to 1 mM completely blocked neuronal death following exposure to 300 $\mu$M NMDA. Inclusion of 1 $\mu$M PBAS significantly reduced neuronal death following continuous exposure to 50 $\mu$M $Fe^{2+}$. $Fe^{2+}$-induced neuronal death was near completely blocked in the presence of 3 $\mu$M PBAS. Free radical neurotoxicity resulting from exposure to 10 mM BSO was blocked by addition of 1 $\mu$M PBAS. PBAS reduced levels of DPPH (table 4), suggesting that PBAS blocked free radical neurotoxicity as a direct antioxidant. Concurrent addition of 100–300 $\mu$M PBAS attenuated $Zn^{2+}$ neurotoxicity (FIG. 8d).

TABLE 4

Anti-oxidant property of PBAS

| | [PBAS], $\mu$M | | | | | | |
|---|---|---|---|---|---|---|---|
| | 0 | 1 | 3 | 10 | 30 | 100 | 300 |
| $A_{517nm}$ | 1.2 ± 0.01 | 1.07 ± 0.07 | 1.01 ± 0.07 | 0.71 ± 0.09* | 0.21 ± 0.04* | 0.15 ± 0.02* | 0.16 ± 0.01* |

PBAS was reacted with 100 uM DPPH dissolved in ethanol for 30 min. Anti-oxidant property was analyzed by measuring changes in DPPH at 517 nm, mean±SEM (n=3 test tubes per condition), after subtracting background value resulting from ethanol alone. Table 4 indicates significant difference from DPPH alone ([PBAS]=0) at P<0.05, using ANOVA and Student-Neuman-Keuls test.

Experimental Example 4

Neuroprotective Effects of NBAS Derivatives (X=CH$_2$)

Figure 9A:
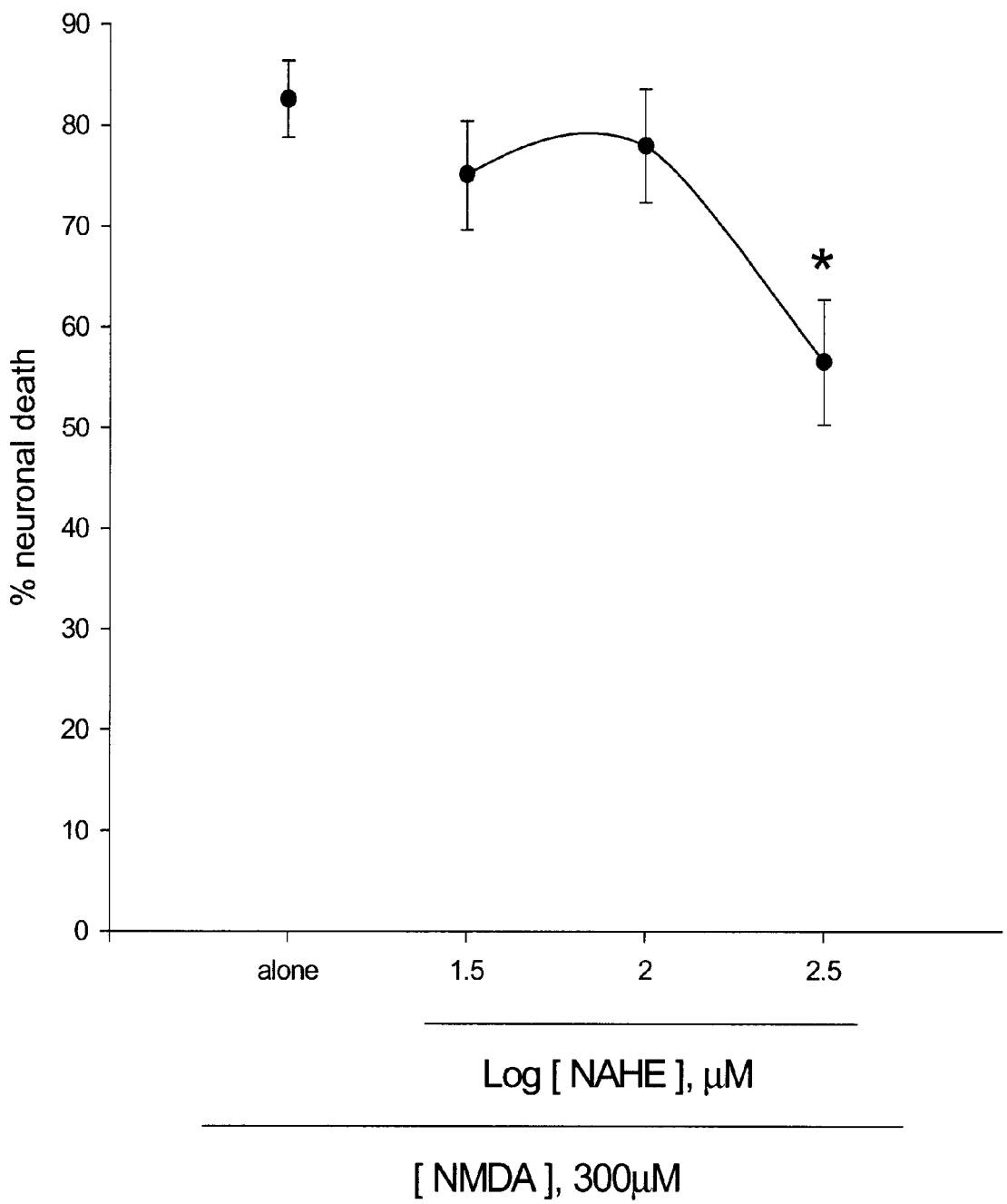
FIG. 9 is a result testing neuroprotective effects of ethyl-5-(4-nitrobenzyl)amino-2-hydroxy ethylbenzoate (NAHE) against neuronal death induced by NMDA (9a) or Fe2+ (9b) in cultured cortical cells.
Figure 9B:
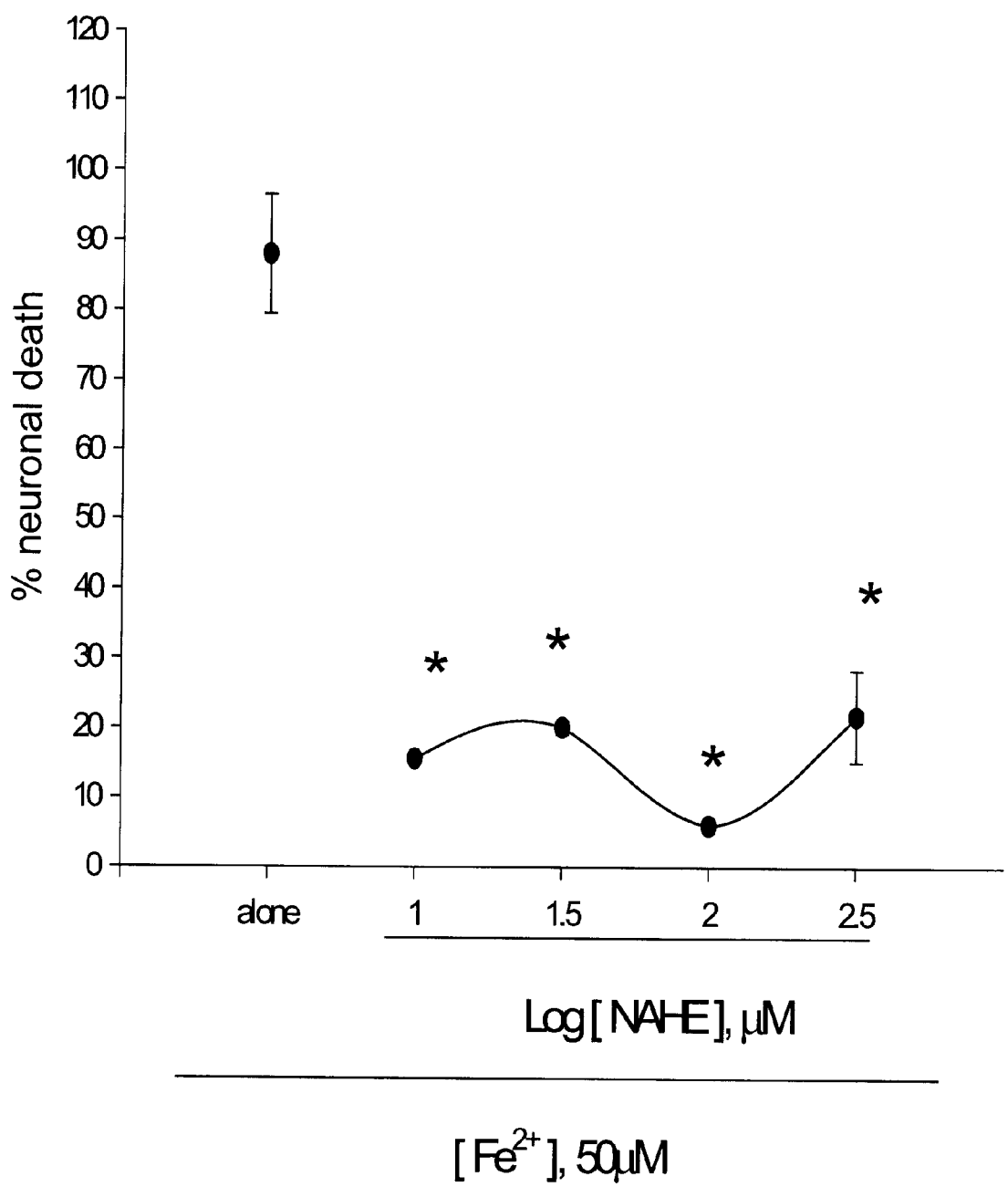

Several derivatives of PBAS such as 5-(4-nitrobenzyl) amino-2-hydroxy ethylbenzoate (NAHE; $R_1$=H, $R_2$=CH$_2$CH$_3$, $R_3$=H), 5-(4-nitrobenzyl)-N-acetylamino-2-hydroxy ethylbenzoate (NNAHE; $R_1$=COCH$_3$, $R_2$=CH$_2$CH$_3$, $R_3$=H), and 5-(4-nitrobenzyl)-N-acetylamino-2-acetoxy ethylbenzoate (NNAAE; $R_1$=COCH$_3$, $R_2$=CH$_2$CH$_3$, $R_3$=COCH$_3$) were synthesized and their neuroprotection action was examined in cortical cell cultures. Mouse cortical cell cultures (DIV 12–14) were exposed to 300 μM NMDA for 10 min (9a) or continuously to 50 μM Fe$^{2+}$ (9b), alone or with inclusion of indicated doses of ethyl-5-(4-nitrobenzyl)amino-2-hydroxy ethylbenzoate (NAHE). Neuronal death was analyzed 24 hr later by measuring levels of LDH released into the medium, mean±SEM (n=10–12 (9a) or n=3–4 (9b) culture wells per condition). The result as shown in FIG. 9 indicates significant difference from relevant control, at p<0.05 using ANOVA and Student-Neuman-Keuls test.

Figure 10A:
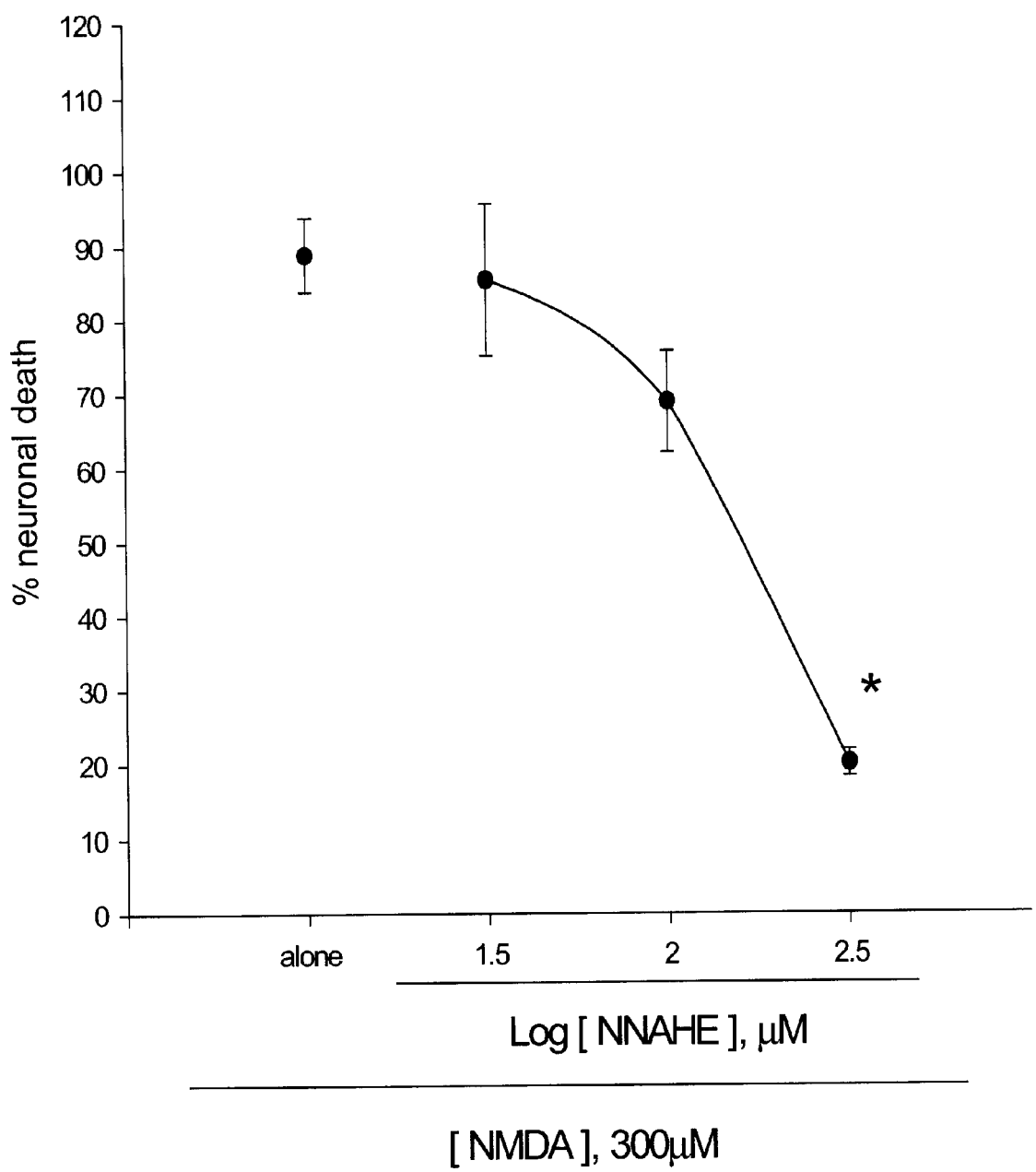
FIG. 10 is a result testing neuroprotective effects of 5-(4-nitrobenzyl)-N-acetylamino-2-hydroxy ethylbenzoate (NNAHE) against neuronal death induced by NMDA (10a) or Fe2+ (10b) in cultured cortical cells.
Figure 10B:
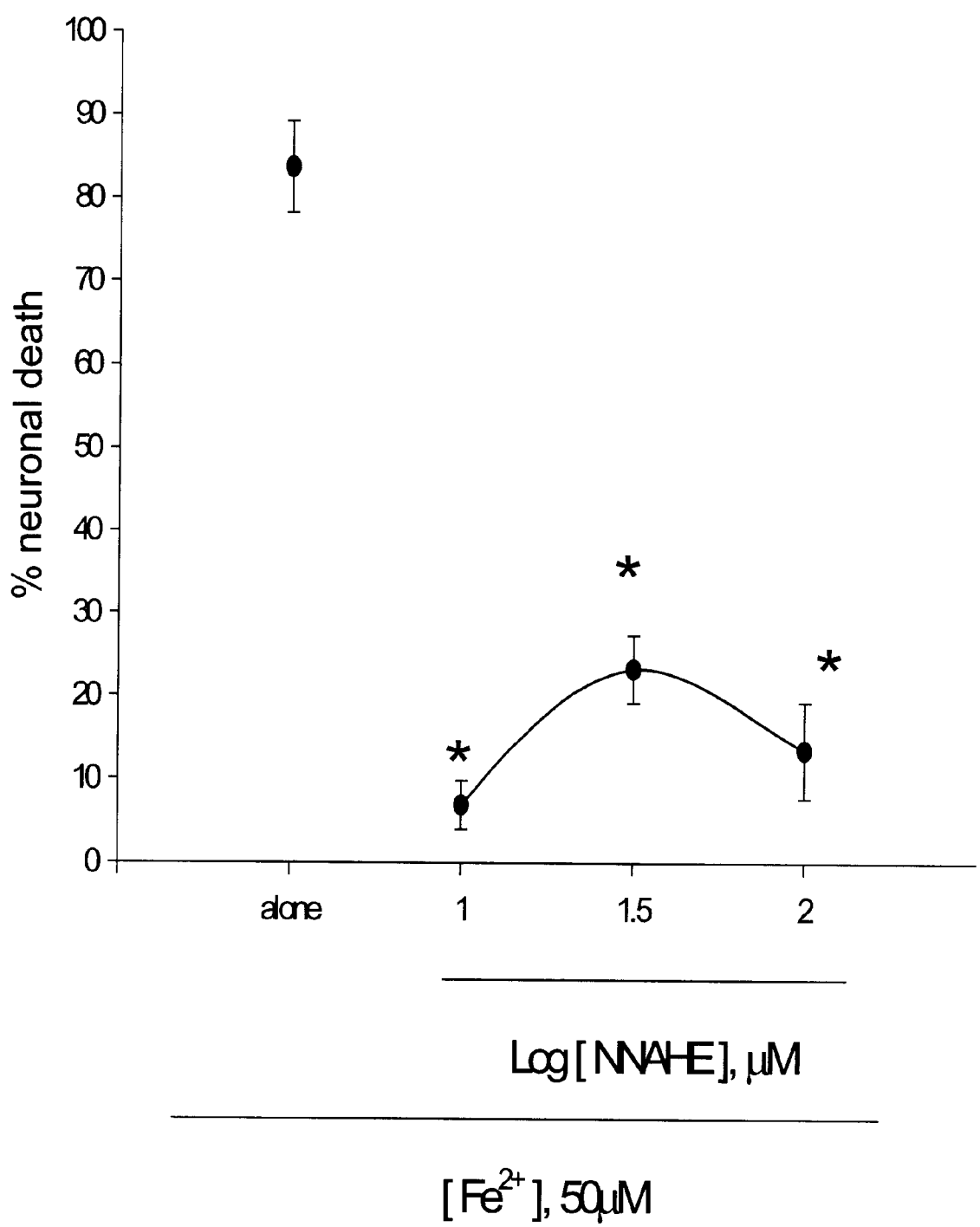

Mouse cortical cell cultures (DIV 12–14) were exposed to 300 μM NMDA for 10 min (10a) or continuously to 50 μM Fe$^{2+}$ (10b), alone or with inclusion of indicated doses of 5-(4-nitrobenzyl)-N-acetylamino-2-hydroxy ethylbenzoate (NNAHE). Neuronal death was analyzed 24 hr later by measuring levels of LDH released into the medium, mean±SEM (n=3–4 (10a) or n=3–4 (10b) culture wells per condition). The result as shown in FIG. 10 indicates significant difference from relevant control, at p<0.05 using ANOVA and Student-Neuman-Keuls test.

Figure 11A:
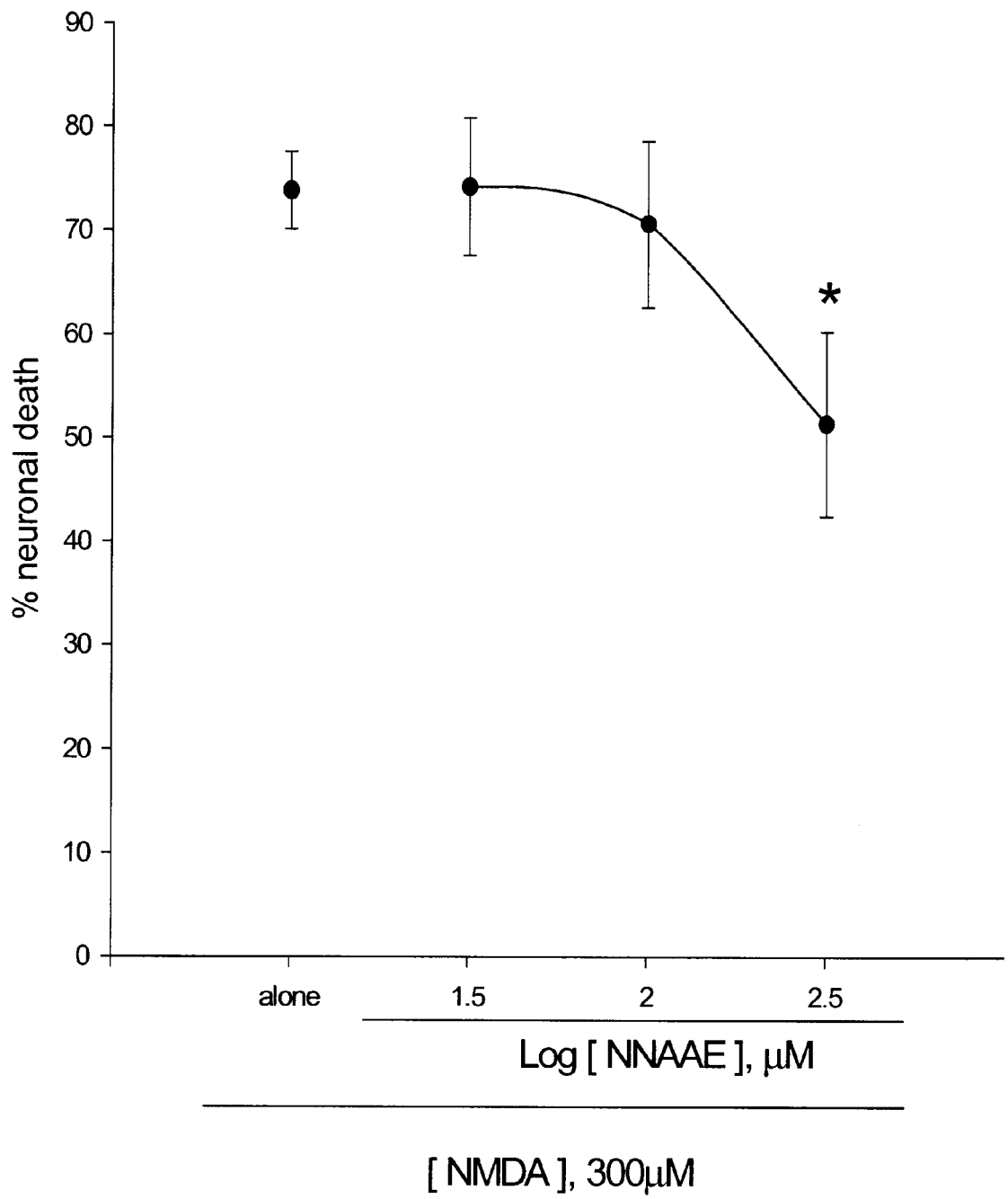
FIG. 11 is a result testing neuroprotective effects of 5-(4-nitrobenzyl)-N-acetylamino-2-acetoxy ethylbenzoate (NNAAE) against neuronal death induced by NMDA (11a) or Fe2+ (11b) in cultured cortical cells.
Figure 11B:
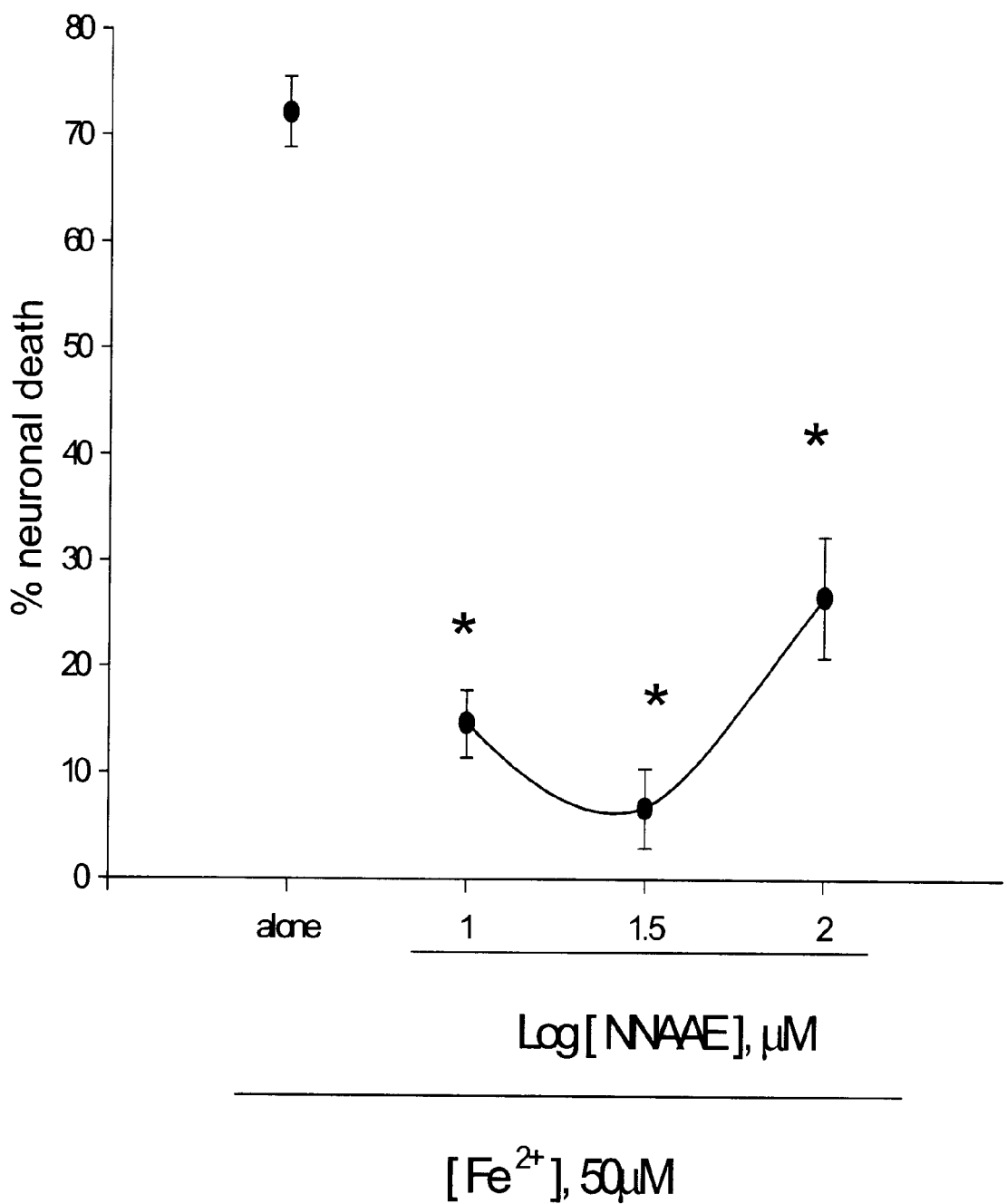

Mouse cortical cell cultures (DIV 12–14) were exposed to 300 μM NMDA for 10 min (11a) or continuously to 50 μM Fe$^{2+}$ (11b), alone or with inclusion of indicated doses of 5-(4-nitrobenzyl)-N-acetylamino-2-acetoxy ethylbenzoate (NNAAE). Neuronal death was analyzed 24 hr later by measuring levels of LDH released into the medium, mean±SEM (n=10–12 (11a), n=7–8 (11b), or n=4 (11c) culture wells per condition). The result as shown in FIG. 11 indicates significant difference from relevant control, at p<0.05 using ANOVA and Student-Neuman-Keuls test. These derivatives attenuated NMDA neurotoxicity at 300 μM (FIGS. 9–11). Inclusion of 10 μM NAHE, NNAHE, or NNAAE blocked Fe$^{2+}$-induced free radical neurotoxicity.

Experimental Example 5

Neuroprotective Effects of NBAS Derivatives (X=CO, SO$_2$, CH$_2$CH$_2$ or CH$_2$CH$_2$CH$_2$)

Figure 12A:
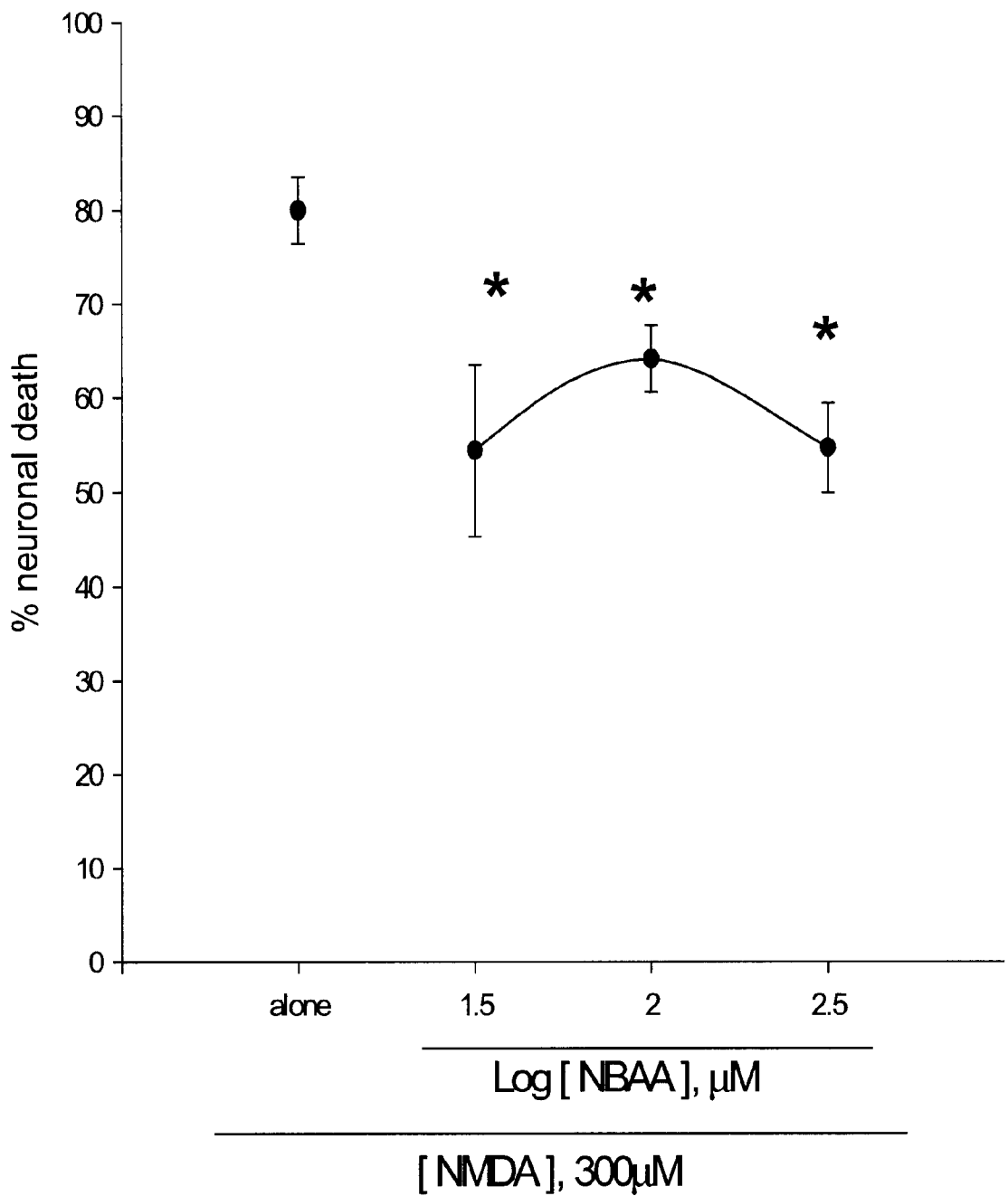
FIG. 12 is a result testing neuroprotective effects of 5-(4-nitrobenzonyl)aminosalicylic acid(NBAA) against neuronal death induced by NMDA (12a) or Fe2+ (12b) in cultured cortical cells.
Figure 12B:
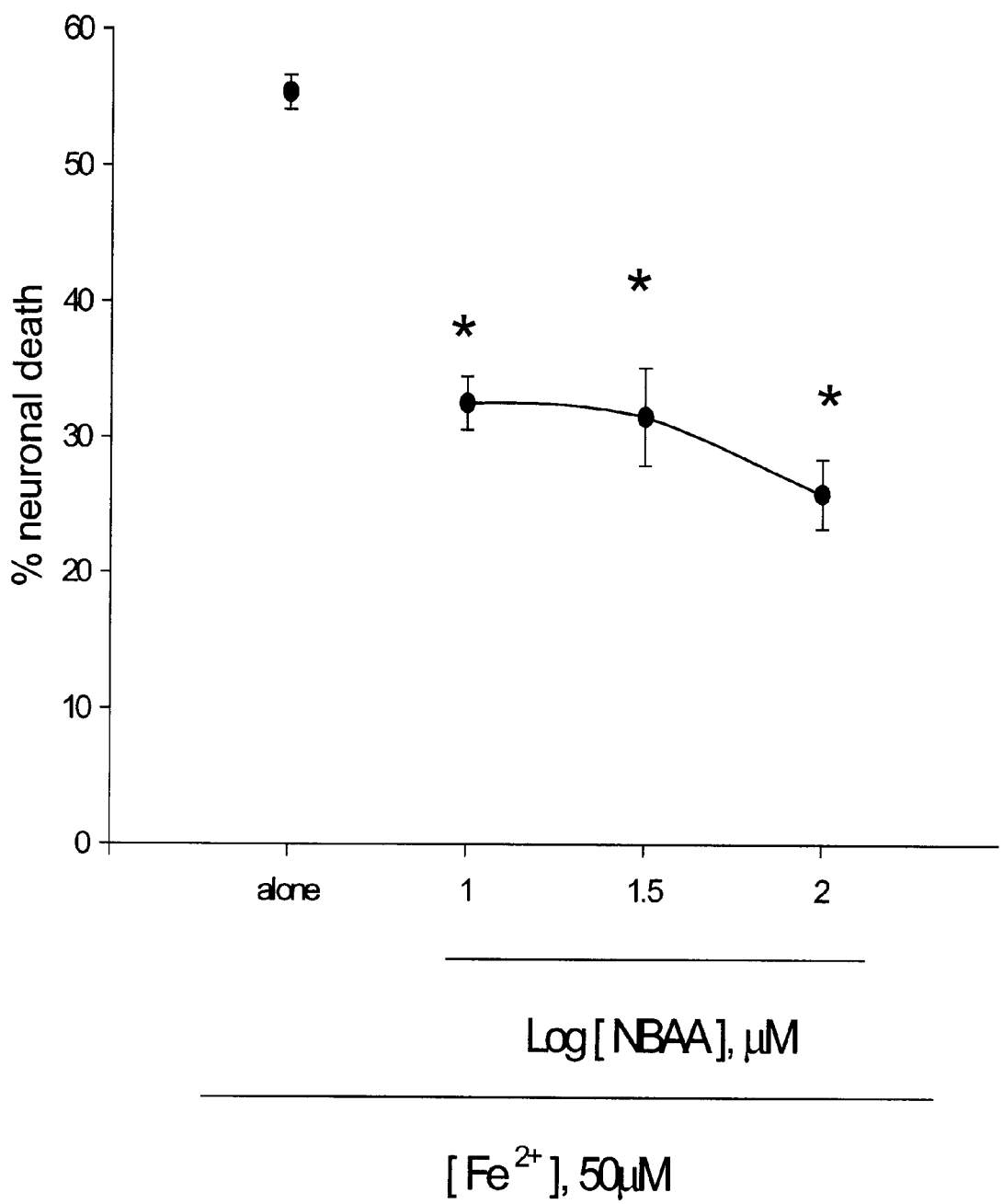

The group of X (CH$_2$) of NBAS was substituted with CO [5-(4-nitrobenzoyl) aminosalicylic acid; NBAA], SO$_2$ [5-(4-nitrobenzenesulfonyl)aminosalicylic acid; NBSAA], CH$_2$CH$_2$ [5-(4-nitrophenethyl)aminosalicylic acid; NPAA], or CH$_2$CH$_2$CH$_2$ [5-[3-(4-nitrophenyl)-n-propyl] aminosalicylic acid; NPPAA]. Mouse cortical cell cultures (DIV 12–14) were exposed to 300 μM NMDA for 10 min (12a) or continuously to 50 μM Fe$^{2+}$ (12b), alone or with inclusion of indicated doses of 5-(4-nitrobenzonyl) aminosalicylic acid(NBAA). Neuronal death was analyzed 24 hr later by measuring levels of LDH released into the medium, mean±SEM (n=7–8 (12a) or n=3–4 (12b) culture wells per condition). The result as shown in FIG. 12 indicates significant difference from relevant control, at p<0.05 using ANOVA and Student-Neuman-Keuls test.

Figure 13A:
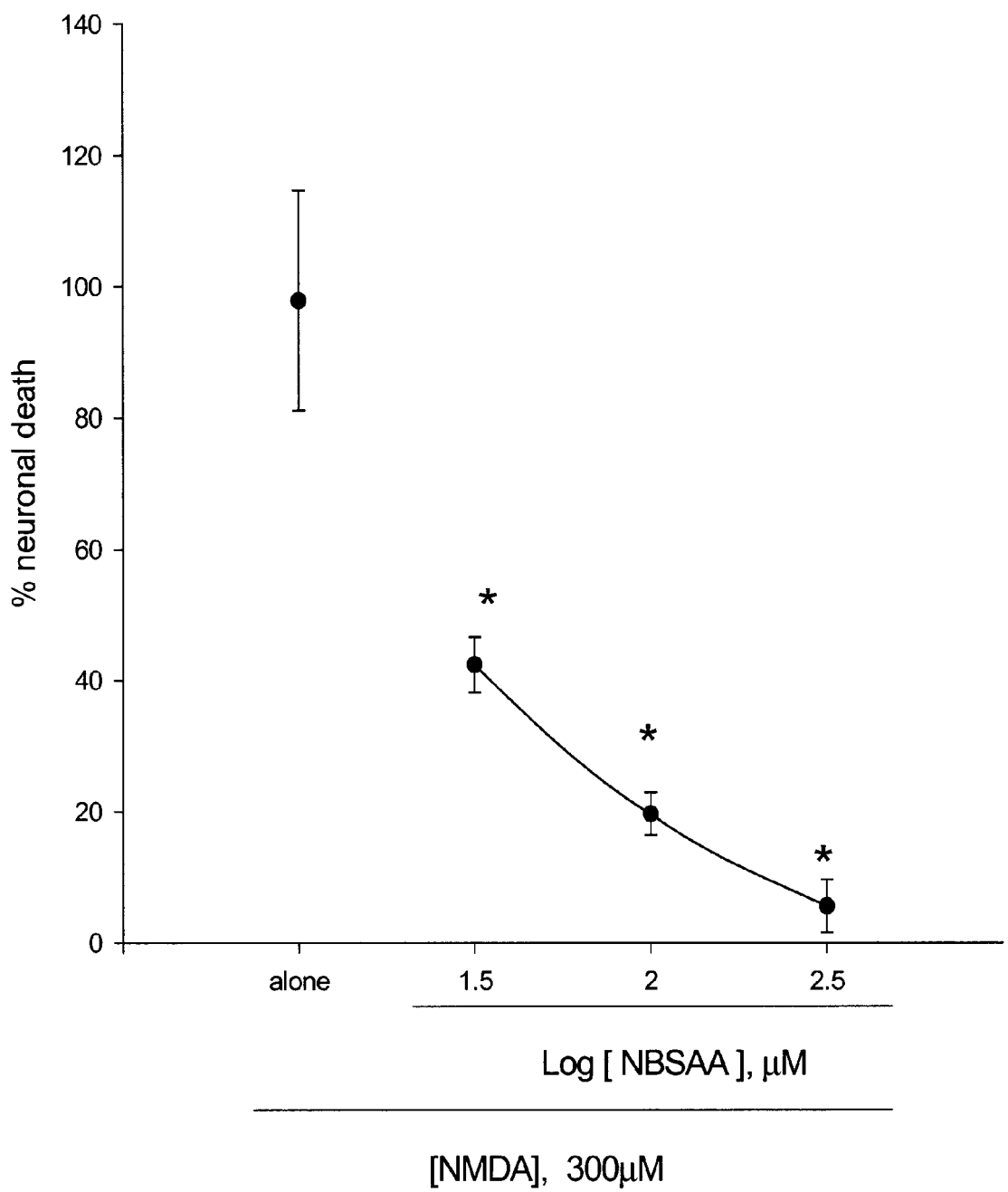
FIG. 13 is a result testing neuroprotective effects of 5-(4-nitrobenzenesulfonyl)aminosalicylic acid (NBSAA) against neuronal death induced by NMDA (13a) or Fe2+ (13b) in cultured cortical cells.
Figure 13B:
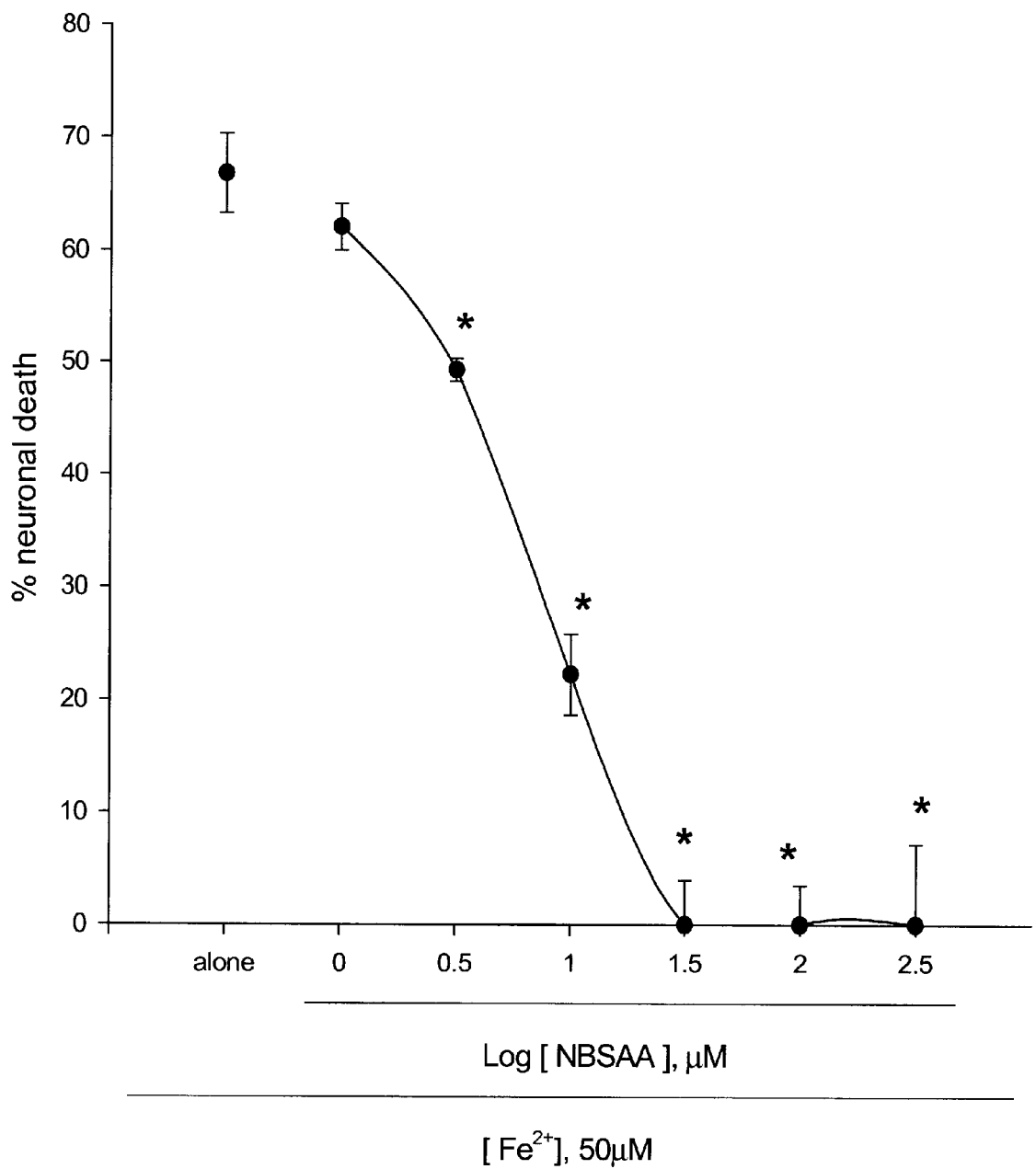

Mouse cortical cell cultures (DIV 12–14) were exposed to 300 μM NMDA for 10 min (13a) or continuously to 50 μM Fe$^{2+}$ (13b) alone or with inclusion of indicated doses of 5-(4-nitrobenzenesulfonyl)aminosalicylic acid(NBSAA). Neuronal death was analyzed 24 hr later by measuring levels of LDH released into the medium, mean±SEM (n=3–4 (13a) or n=2–8 (13b) culture wells per condition). The result as shown in FIG. 13 indicates significant difference from relevant control, at p<0.05 using ANOVA and Student-Neuman-Keuls test.

Figure 14A:
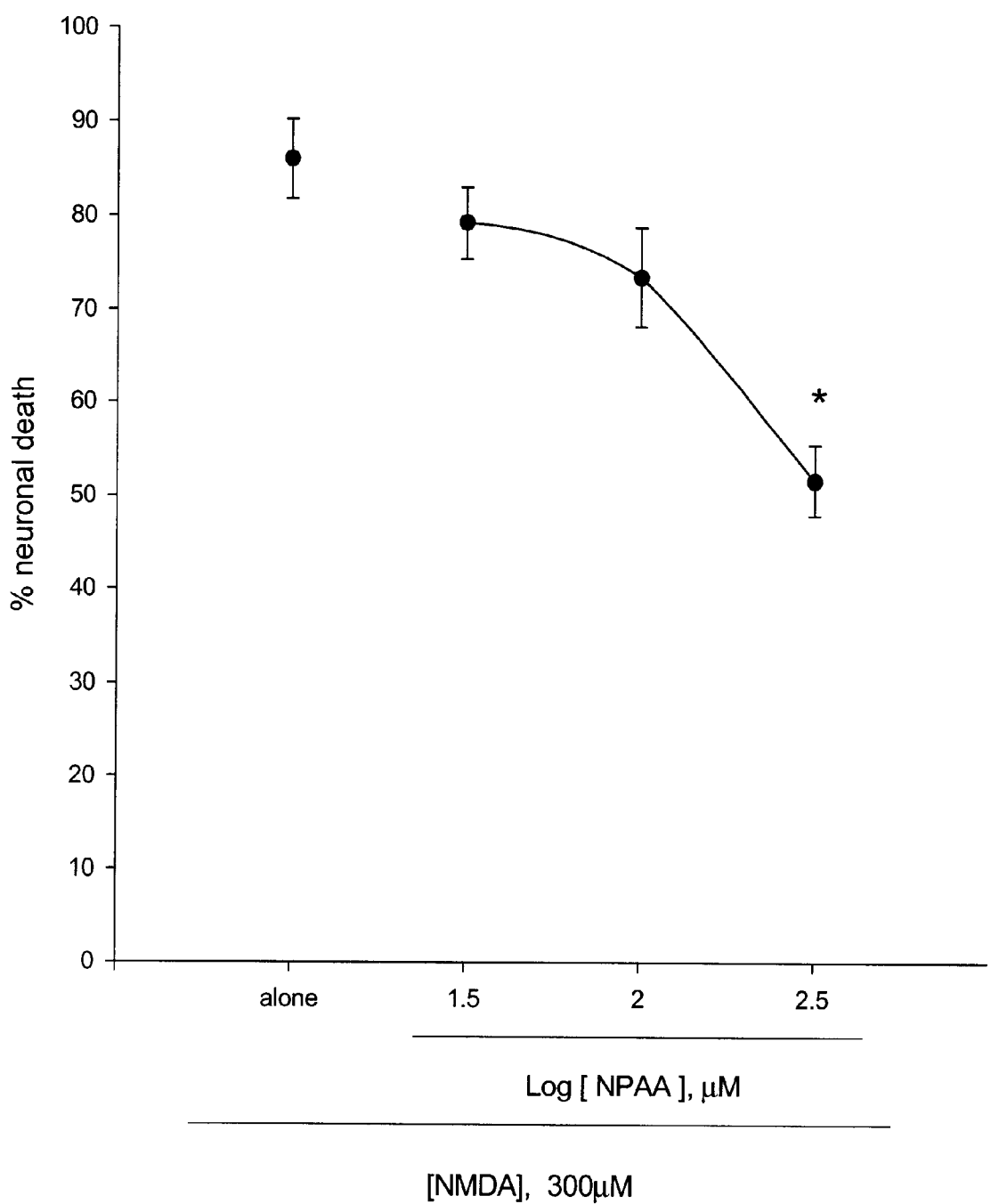
FIG. 14 is a result testing neuroprotective effects of 5-[2-(4-nitrophenyl)-ethyl]aminosalicylic acid (NPAA) against neuronal death induced by NMDA (14a) or Fe2+ (14b) in cultured cortical cells.
Figure 14B:
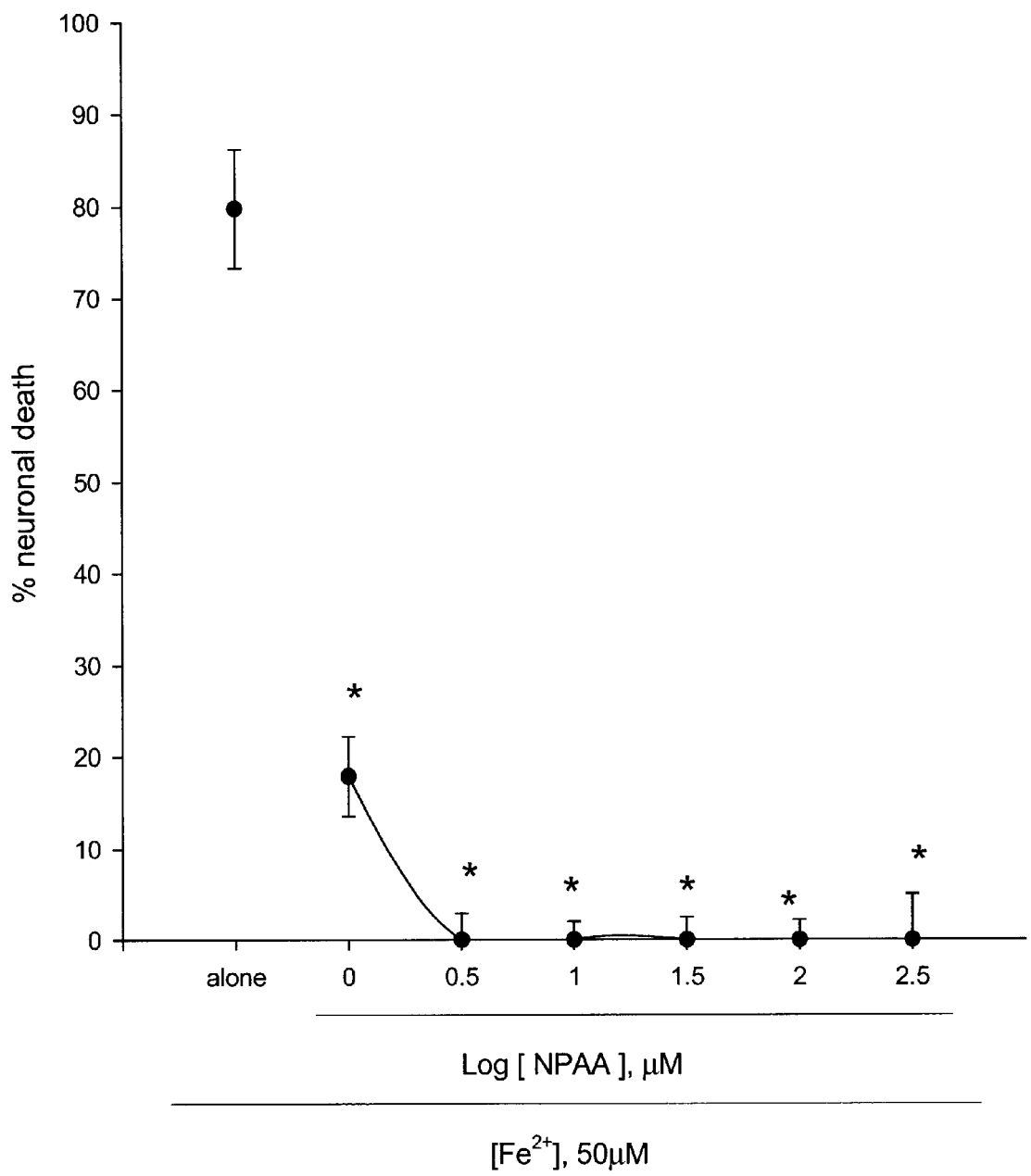

Mouse cortical cell cultures (DIV 12–14) were exposed to 300 μM NMDA for 10 min (14a) or continuously to 50 μM Fe$^{2+}$ (14b), alone or with inclusion of indicated doses of 5-[2-(4-nitrophenyl)-ethyl]aminosalicylic acid(NPAA). Neuronal death was analyzed 24 hr later by measuring levels of LDH released into the medium, mean±SEM (n=4 (14a) or n=4–8 (14b) culture wells per condition). The result as shown in FIG. 14 indicates significant difference from relevant control, at p<0.05 using ANOVA and Student-Neuman-Keuls test.

Figure 15A:
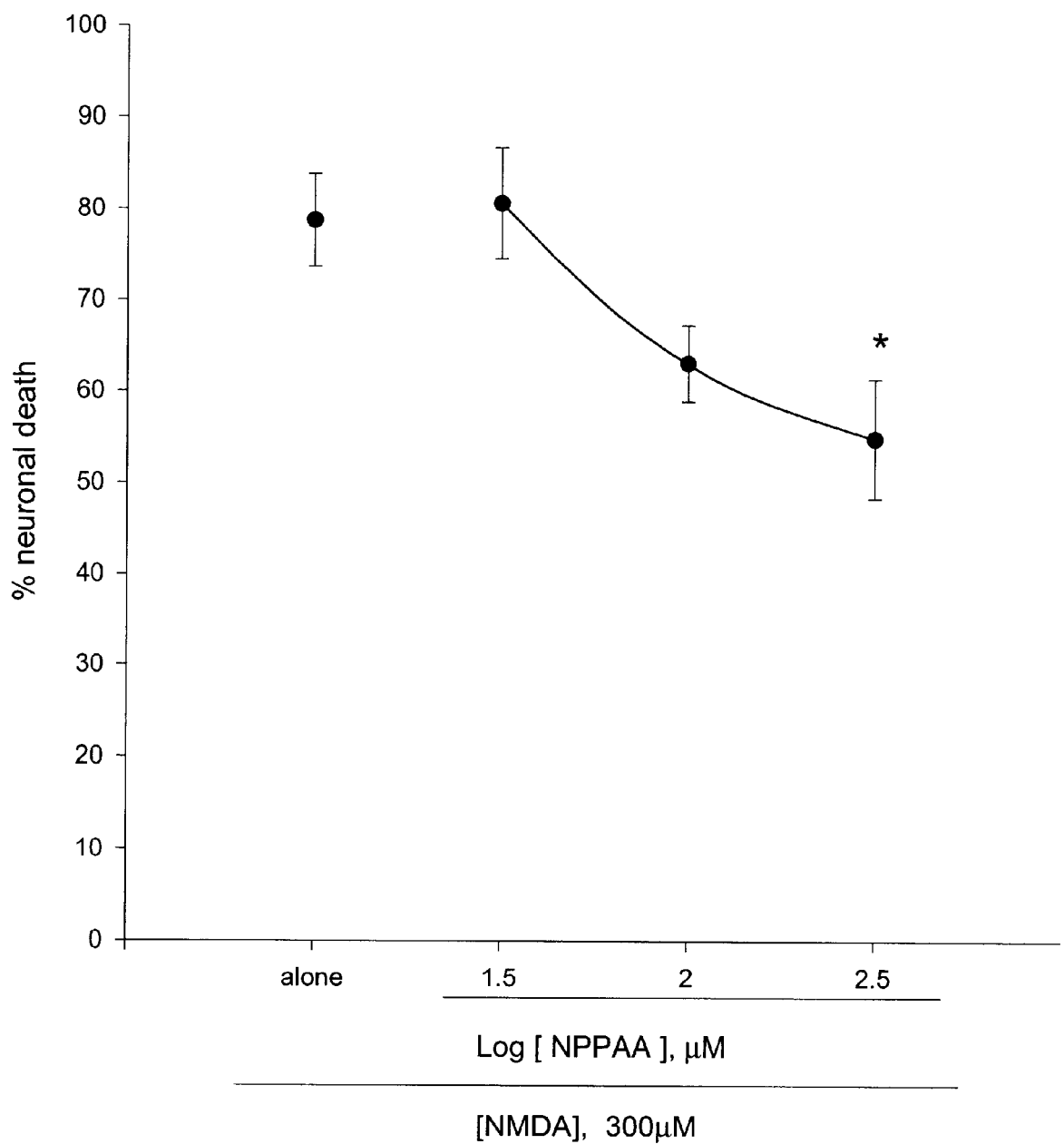
FIG. 15 is a result testing neuroprotective effects of 5-[3-(4-nitrophenyl)-n-propyl]aminosalicylic acid (NPPAA) against neuronal death induced by NMDA (15a) or Fe2+ (15b) in cultured cortical cells.
Figure 15B:
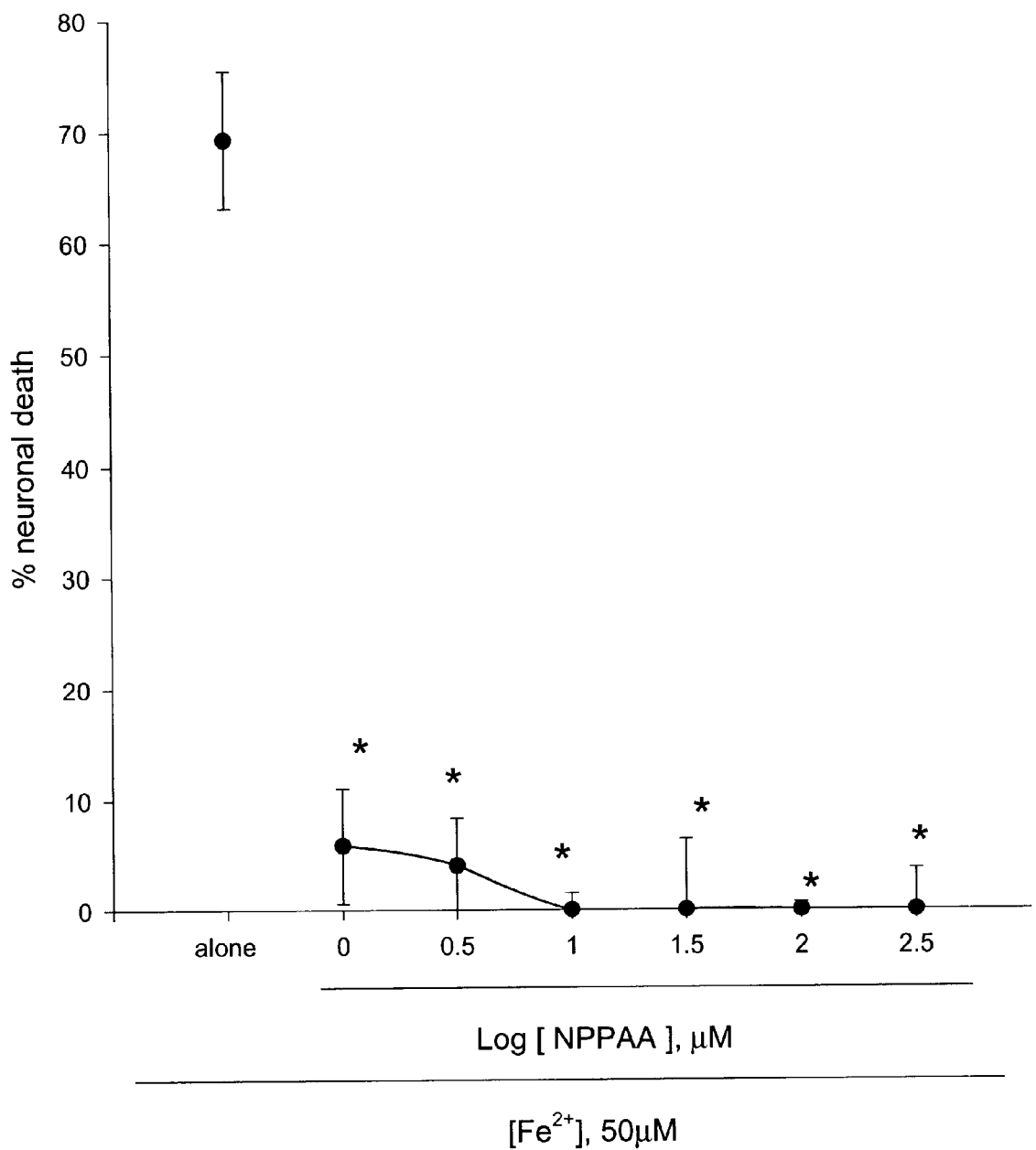

Mouse cortical cell cultures (DIV 12–14) were exposed to 300 μM NMDA for 10 min (15a) or continuously to 50 μM Fe$^{2+}$ (15b), alone or with inclusion of indicated doses of 5-[3-(4-nitrophenyl)-n-propyl]aminosalicylic acid (NPPAA). Neuronal death was analyzed 24 hr later by measuring levels of LDH released into the medium, mean±SEM (n=4 (15a) or n=3–8 (15b) culture wells per condition). The result as shown in FIG. 15 indicates significant difference from relevant control, at p<0.05 using ANOVA and Student-Neuman-Keuls test. NBAA at a dose of 30 μM significantly attenuated NMDA neurotoxicity. However, its protective effect against NMDA was not further increased up to doses of 300 μM (FIG. 12a). Interestingly, inclusion of 30–300 μM NBSAA attenuated NMDA neurotoxicity in a dose-dependent manner (FIG. 13a). With inclusion of 300 μM NBSAA, 90–100% neuronal death following exposure to 300 μM NMDA was markedly reduced. NBAA and NBSAA were still neuroprotective against Fe$^{2+}$ injury but weaker than NBAS in reducing free radical neurotoxicity (FIGS. 12 and 13; Table 5).

Substitution of CH$_2$ for X with CH$_2$CH$_2$ or CH$_2$CH$_2$CH$_2$ reduced protective potency of NBAS against NMDA neurotoxicity. Administration of 300 μM NPAA or NPPAA slightly reduced NMDA-induced neuronal death in cortical neurons (FIGS. 14 and 15). In contrast, NPAA or NPPAA turned out to be more effective than NBAS in blocking free radical neurotoxicity as shown by complete blockade of Fe$^{2+}$-induced neuronal death in the presence of 1 μM NPAA or NPPAA.

TABLE 5

Anti-oxidant property of NBAS derivatives

| | Reactants | | | | |
|---|---|---|---|---|---|
| | DPPH alone | DPPH + NBAA | DPPH + NBSAA | DPPH + NPAA | DPPH + NPPAA |
| $A_{517nm}$ | 1.2 ± 0.01 | 0.42 ± 0.22* | 0.15 ± 0.05* | 0.09 ± 0.01* | 0.09 ± 0.02* |

NBAS derivatives (100 μM for each) were reacted with 100 μM DPPH dissolved in ethanol for 30 min. Anti-oxidant property was analyzed by measuring changes in DPPH at 517 nm, mean±SEM (n=3 test tubes per condition), after subtracting background value resulting from ethanol alone. Table 5 indicates significant difference from DPPH alone at P<0.05, using ANOVA and Student-Neuman-Keuls test.

The above results show that the compounds of Formula (I) may be employed efficiently to prevent neurodegenerative diseases in association with excitotoxicity, $Zn^{2+}$ neurotoxicity and free radical neurotoxicity.

Administration of compounds within Formula (I) to humans can be by any technique capable of introducing the compounds into the bloodstream of a human patient or mammals, including oral administration, and by intravenous, intramuscular and subcutaneous injections The mammals include, but not limited to, cats, dogs, poultry, cattle and the like.

Compounds indicated for prophylactic therapy will preferably be administered in a daily dose generally in a range from about 0.1 mg to about 20 mg per kilogram of body weight per day. A more preferred dosage will be a range from about 0.2 mg to about 10 mg per kilogram of body weight. Most preferred is a dosage in a range from about 0.5 to about 5 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be performed by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a disposition of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound represented by the following formula:

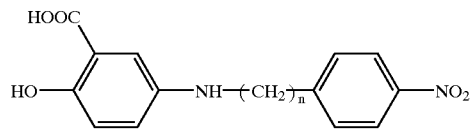

wherein, n is an integer of 2 or 3.

* * * * *